(12) United States Patent
Kesseler et al.

(10) Patent No.: US 6,998,258 B1
(45) Date of Patent: Feb. 14, 2006

(54) L-PANTOLACTONE-HYDROLASE AND A METHOD FOR PRODUCING D-PANTOLACTONE

(75) Inventors: Maria Kesseler, Mannheim (DE); Bernhard Hauer, Fussgönheim (DE); Thomas Friedrich, Darmstadt (DE); Ralf Mattes, Stuttgart (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 316 days.

(21) Appl. No.: 10/111,451

(22) PCT Filed: Oct. 20, 2000

(86) PCT No.: PCT/EP00/10320

§ 371 (c)(1),
(2), (4) Date: Apr. 25, 2002

(87) PCT Pub. No.: WO01/32890

PCT Pub. Date: May 10, 2001

(30) Foreign Application Priority Data

Oct. 29, 1999 (DE) .............................. 199 52 501
Jun. 19, 2000 (DE) .............................. 100 29 194

(51) Int. Cl.
*C12N 9/14* (2006.01)
*C12N 15/55* (2006.01)
*C12P 7/26* (2006.01)

(52) U.S. Cl. ................ 435/195; 435/320.1; 435/252.3; 435/148; 536/23.2

(58) Field of Classification Search ................ 435/195, 435/320.1, 252.3, 148; 536/23.2
See application file for complete search history.

(56) References Cited

U.S. PATENT DOCUMENTS

| | | | | |
|---|---|---|---|---|
| 5,275,949 A | | 1/1994 | Sakamoto et al. | 435/280 |
| 5,372,940 A | * | 12/1994 | Sakamoto et al. | 435/195 |
| 6,395,529 B1 | * | 5/2002 | Berka et al. | 435/197 |
| 6,406,898 B1 | * | 6/2002 | Sakamoto et al. | 435/195 |
| 6,756,220 B1 | * | 6/2004 | Berka et al. | 435/197 |

FOREIGN PATENT DOCUMENTS

| | | |
|---|---|---|
| CA | 2064676 | 10/1992 |
| DE | 40 05 150 | 8/1991 |
| DE | 41 26 580 | 2/1993 |
| DE | 41 39987 | 4/1993 |
| EP | 504 421 | 9/1992 |
| EP | 507 278 | 10/1992 |
| EP | 528 256 | 2/1993 |
| EP | 436 730 | 10/1995 |
| EP | 794 251 | 9/1997 |
| WO | 92/06182 | 4/1992 |
| WO | 94/09175 | 4/1994 |
| WO | 97/10341 | 3/1997 |
| WO | 00/28043 | 5/2000 |

OTHER PUBLICATIONS

Ullmann's Enc. of Ind.Chem.vol. A27, 1996, 559-566.
Enzyme and Microbial Tech. vol. 10,No. 7, Jul. 1988 689-690, Glanzer, et al.
Appl.Micro.Bio. 1995, 44:333-338, Kataoka et al.
Optical resolution of racemic . . . Kataoka et al., Enzy Micro.Tech. 19:307-310, 1996.
Lactone-ring-cleaving . . . Kobayashi et al., 12787-12792 1981, PNAS.
Purification and characterization . . . Shimizu et al., Eur.J. Biochem. 209, 383-390 (1992).
OpticalResolution of Pantolactone . . . Shimizu et al., 650-658, Ann. N.Y. Acad. Sci. 759 (1996).
Microbial and Enzymatic . . . Yamada et al., (1988) 622-642, Angen Chem Int. Ed. Engl 27.
Stereoselective synthessis . . . Shimizu et al. Chem. Asp. Enz. Biotech (1990) 151-163.
J. Bio. Chem., Aug. 25, 1988, vol. 263, No. 24, Shimizu et al., 12077-12084.
Purification and characterization . . . Kataoka et al., Eur.J. Biochm. 204, 799-806 (1992).
Derwent Abst. JP 09308497.
Derwent Abst. JP 11056356.
Chimia, vol. 47 (1993) Yamada, 69-74.
J57152-895-Derwent abstract.
The Enantiomeric ratio . . . Straathol et al., 559-571 (1997), Enz. Microbial Tech.
Nucleic acid hydridisation, Edited by Hames et al. (1985) (contents only).
Jr. of Molecular Bio., vol. 48, 443-453, (1970) Needleman, et al.
Gene, vol. 96, No. 1, 1990, Inoue et al. 23-28.
XP-002161908 (1980).
XP-002161909 (1988).
XP-002161910 (1988).

* cited by examiner

Primary Examiner—Charles L. Patterson, Jr.
(74) Attorney, Agent, or Firm—Novak Druce & Quigg

(57) ABSTRACT

The present invention relates to proteins which have an enzymatic activity for hydrolyzing L-pantolactone. The invention further relates to nucleic acids which code for these proteins, to nucleic acid constructs, vectors, genetically modified microorganisms and to a process for preparing D-pantolactone.

20 Claims, 11 Drawing Sheets

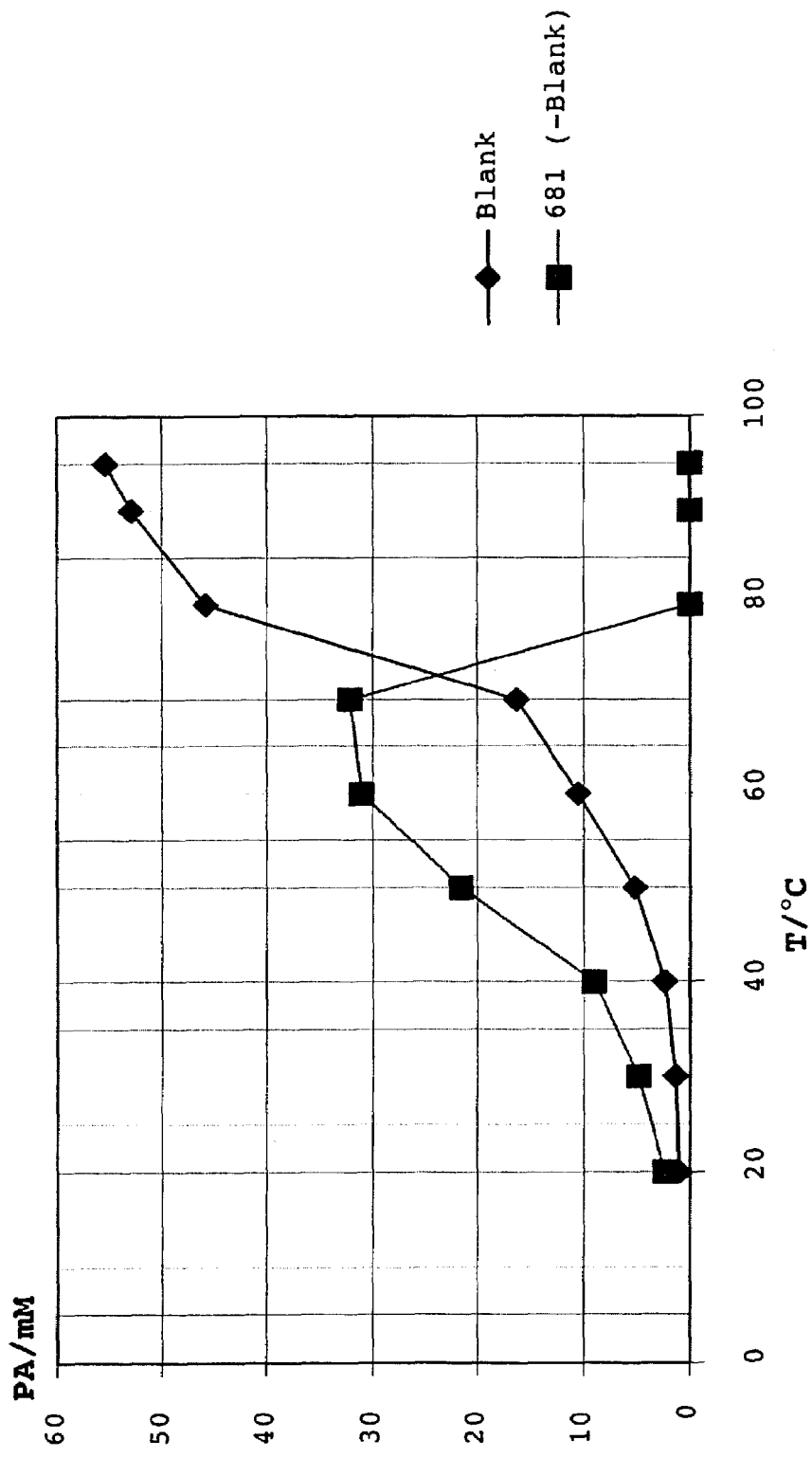
Figure 1a Temperature optimum for L-pantolactone hydrolase from Burkholderia caryophylli Lu681

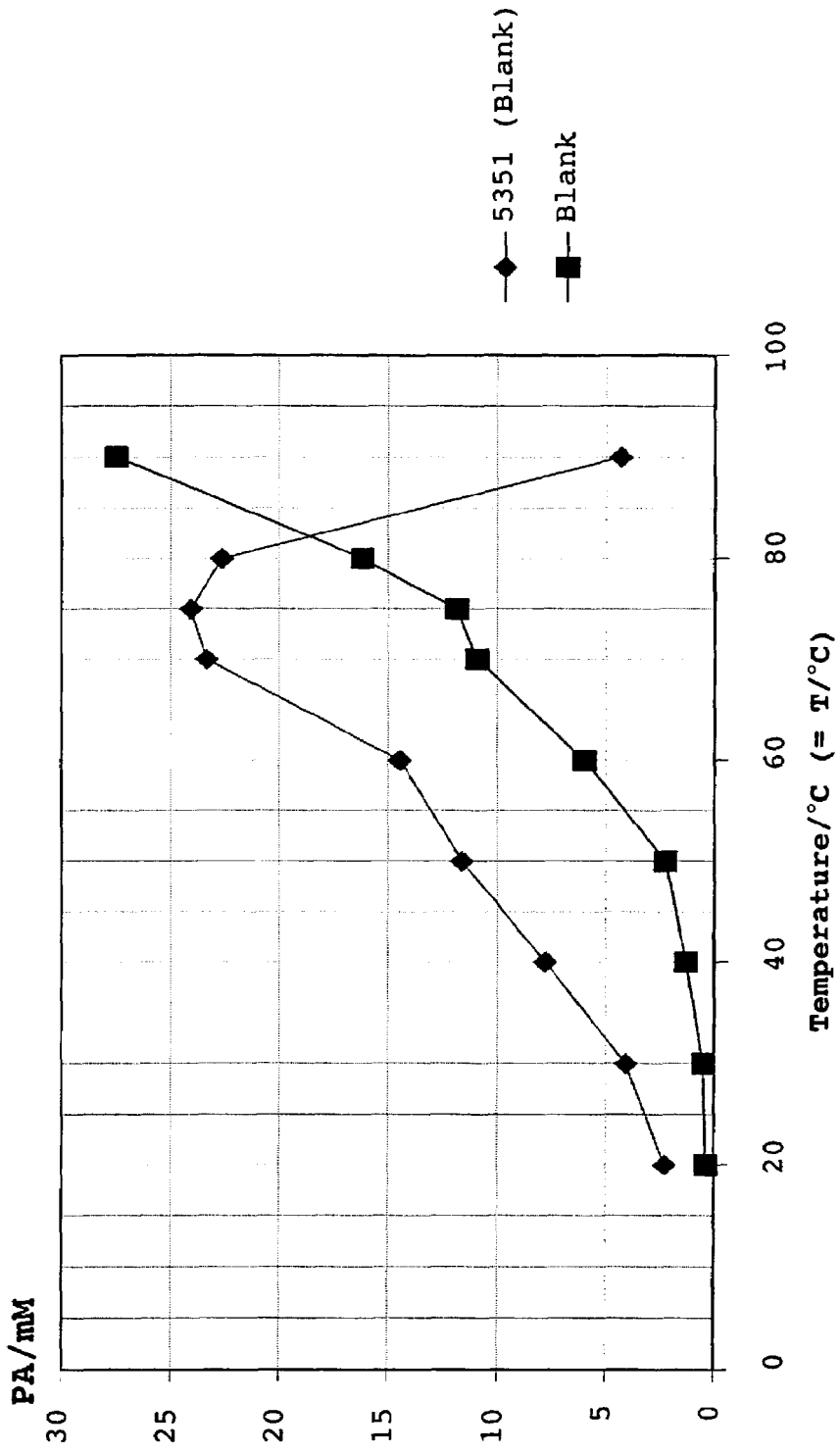
Figure 1b Temperature optimum for L-pantolactone hydrolase from Agrobacterium radiobacter Lu5351

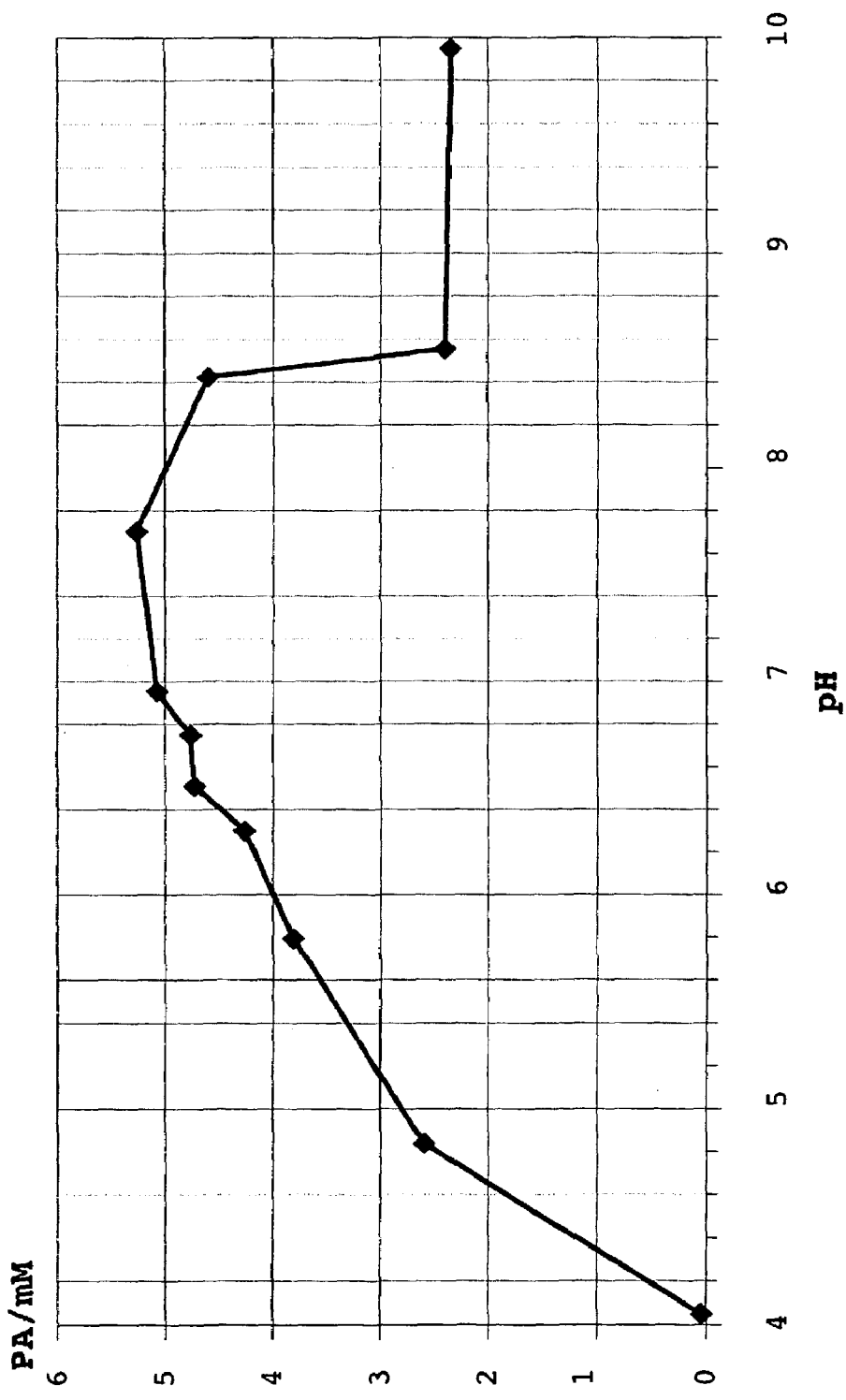
Figure 2a: pH-optimum for L-pantolactone hydrolase from Burkholderia caryophylli Lu681

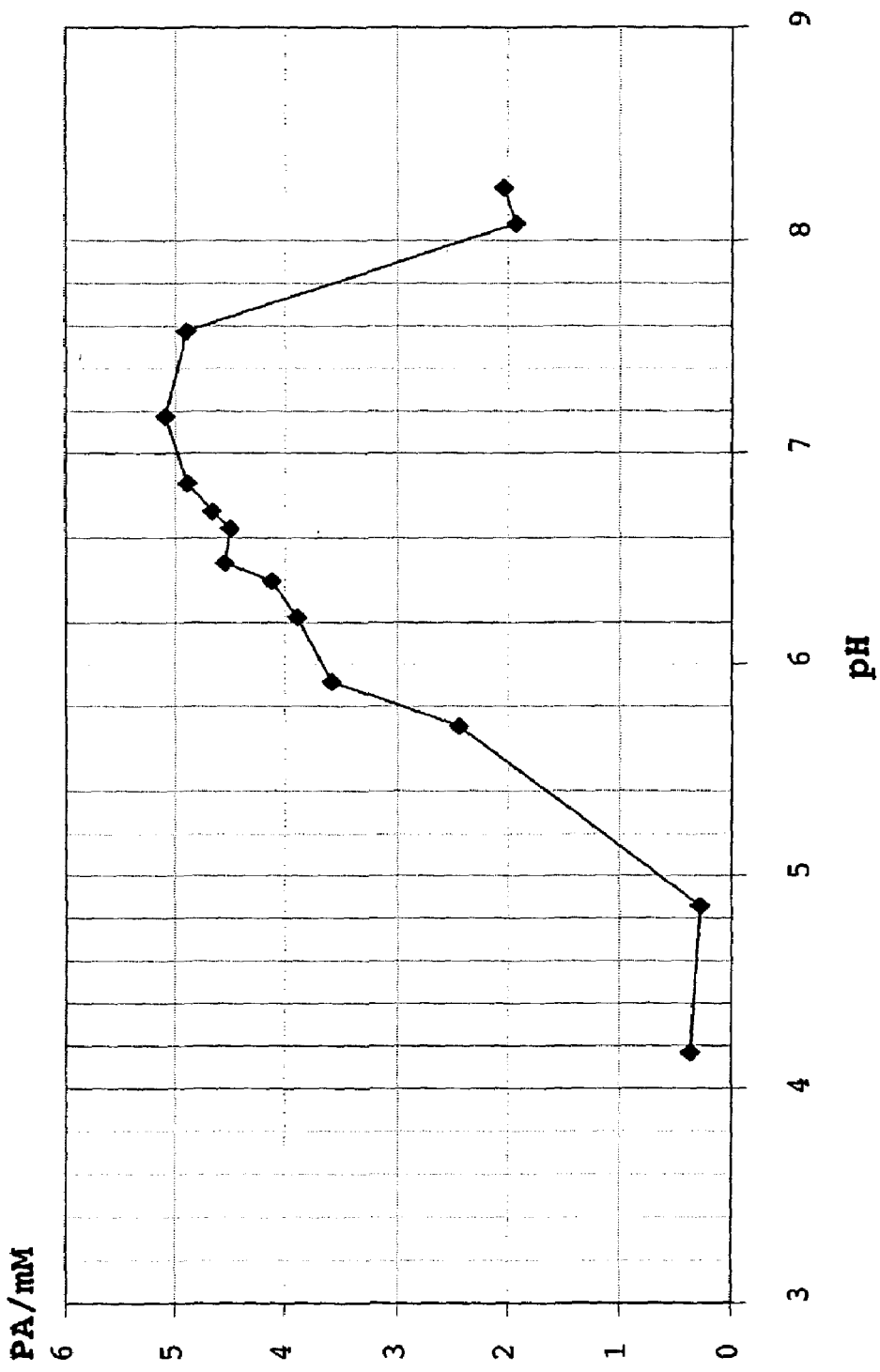
Figure 2b pH-optimum for L-pantolactone hydrolase from Agrobacterium radiobacter Lu5351

Figure 3: Restriction map of pKS+681
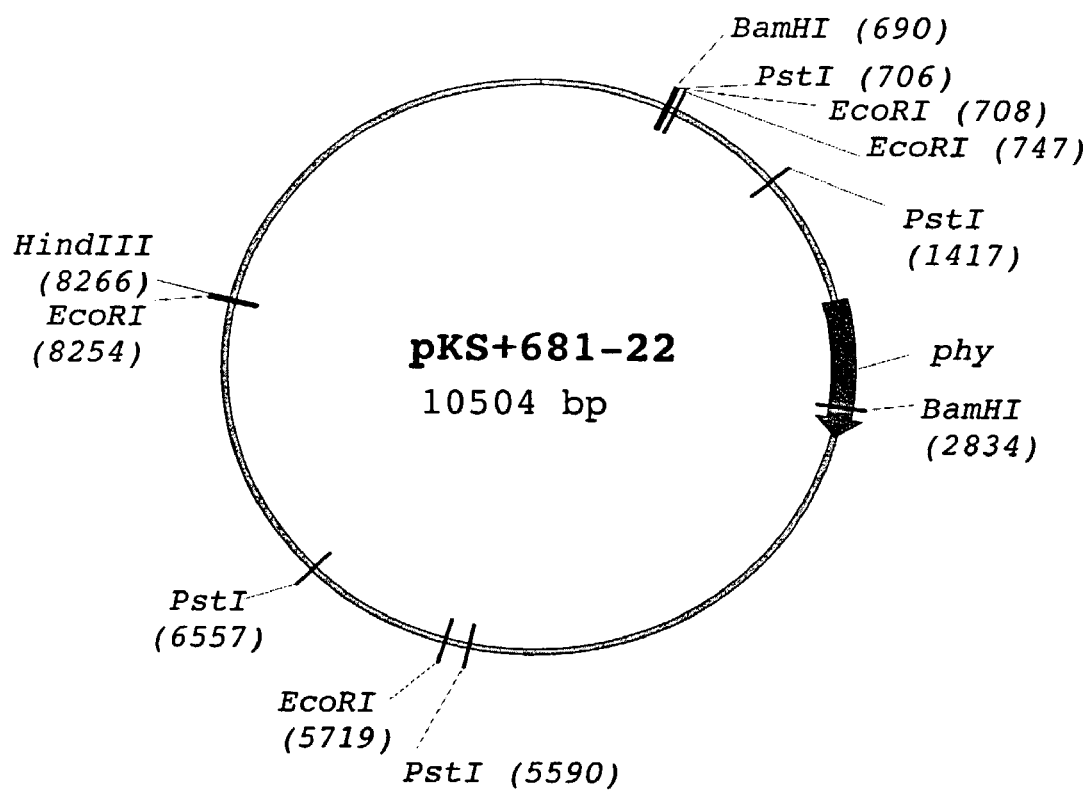

Figure 4: Restriction map of pKK681
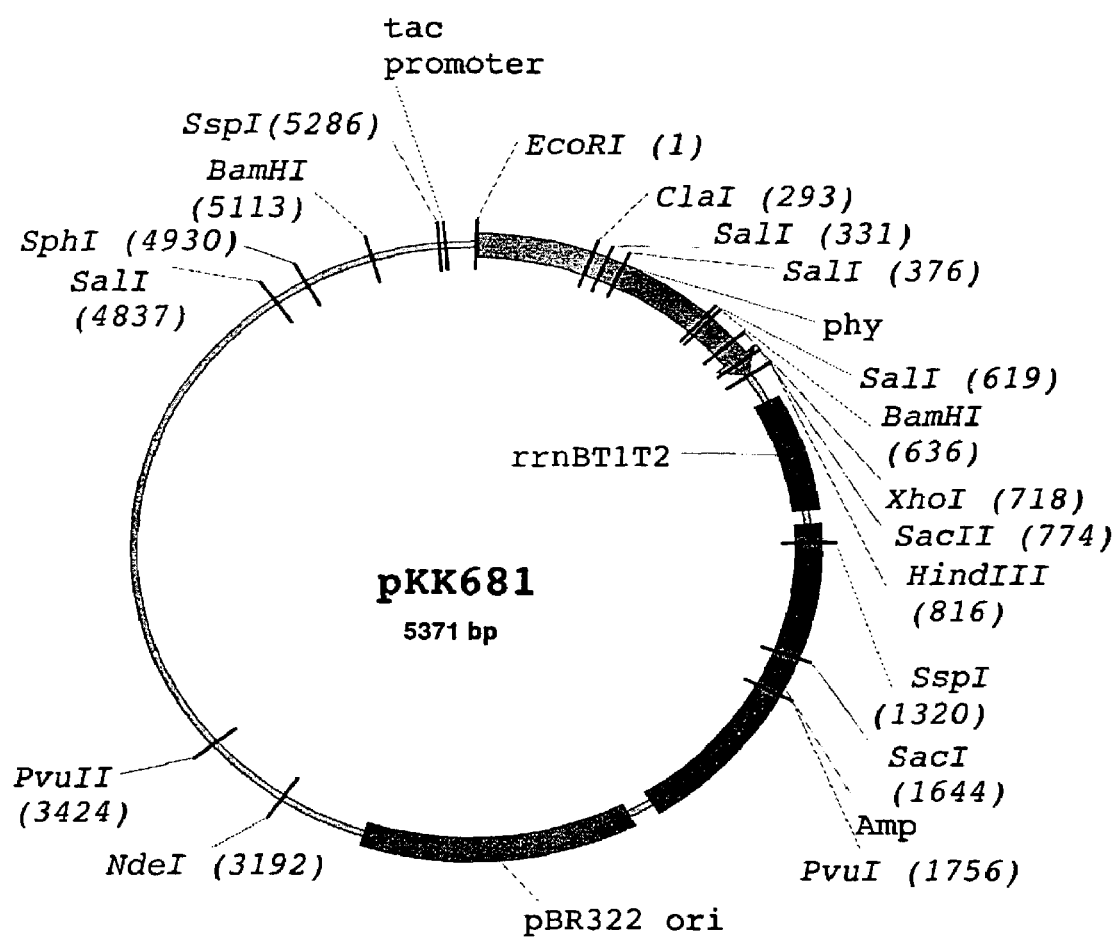

Figure 5: Restriction map of pDHE681
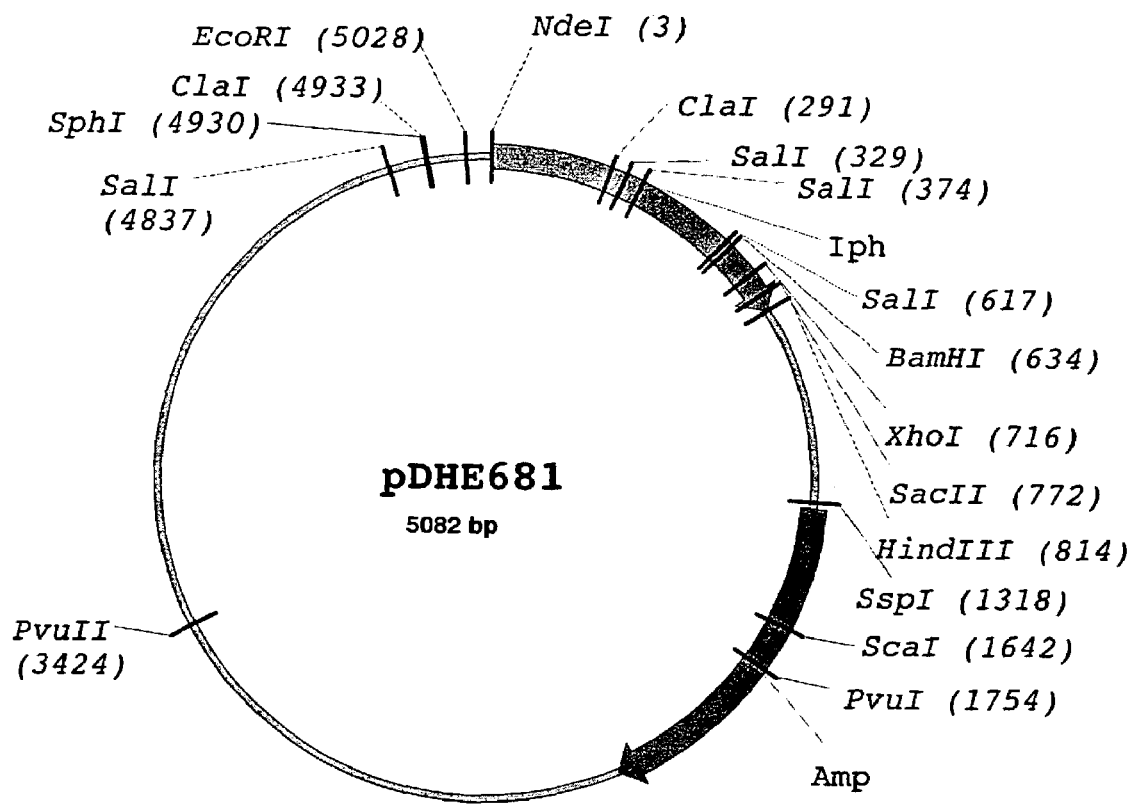

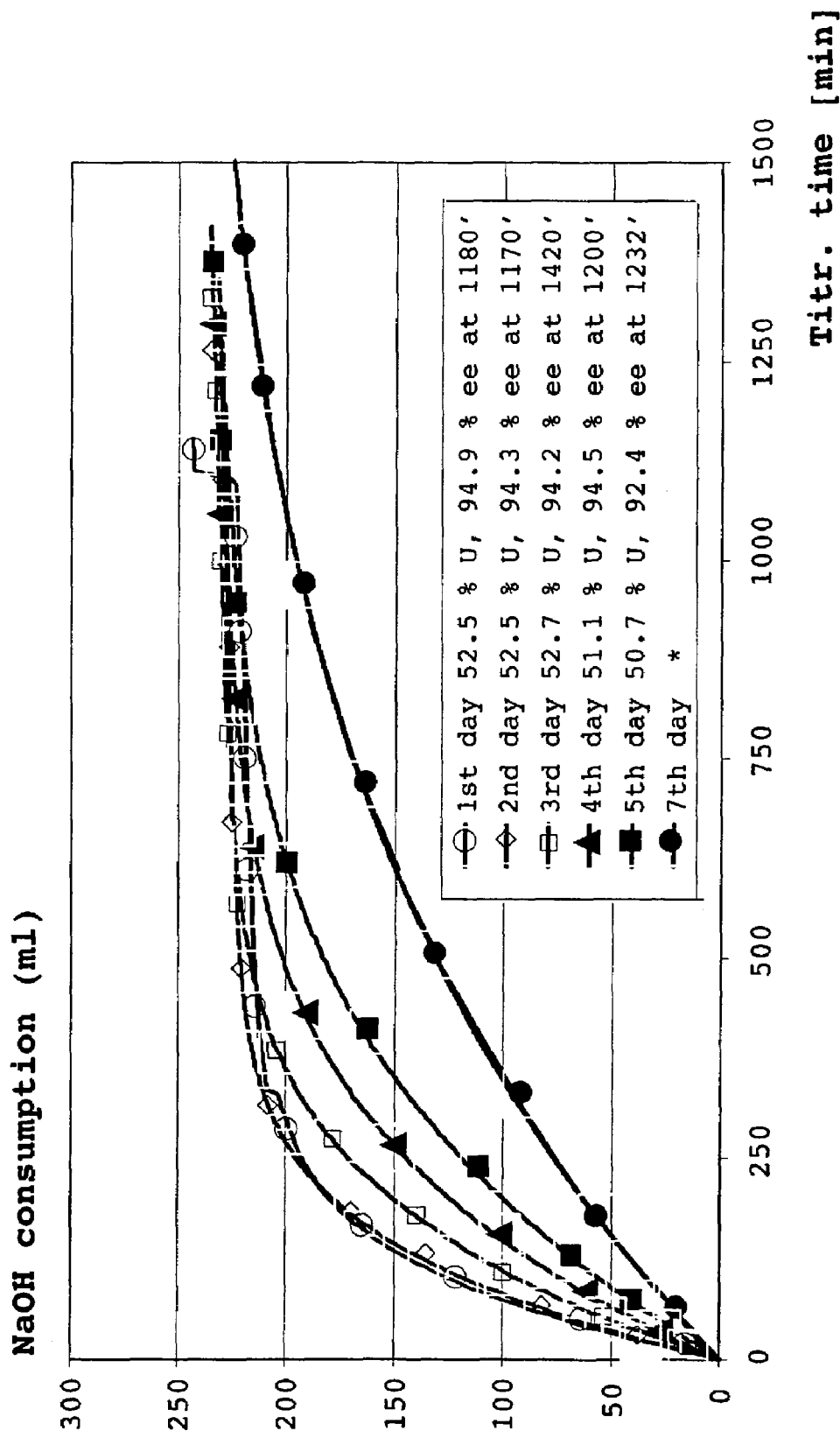
Figure 7: Lu9981 homogenate useful life

Figure 8: Useful life of L-pantolactone hydrolase immobilized on Engergit C, 80.8 U/g, 8.6% w/v in the batch
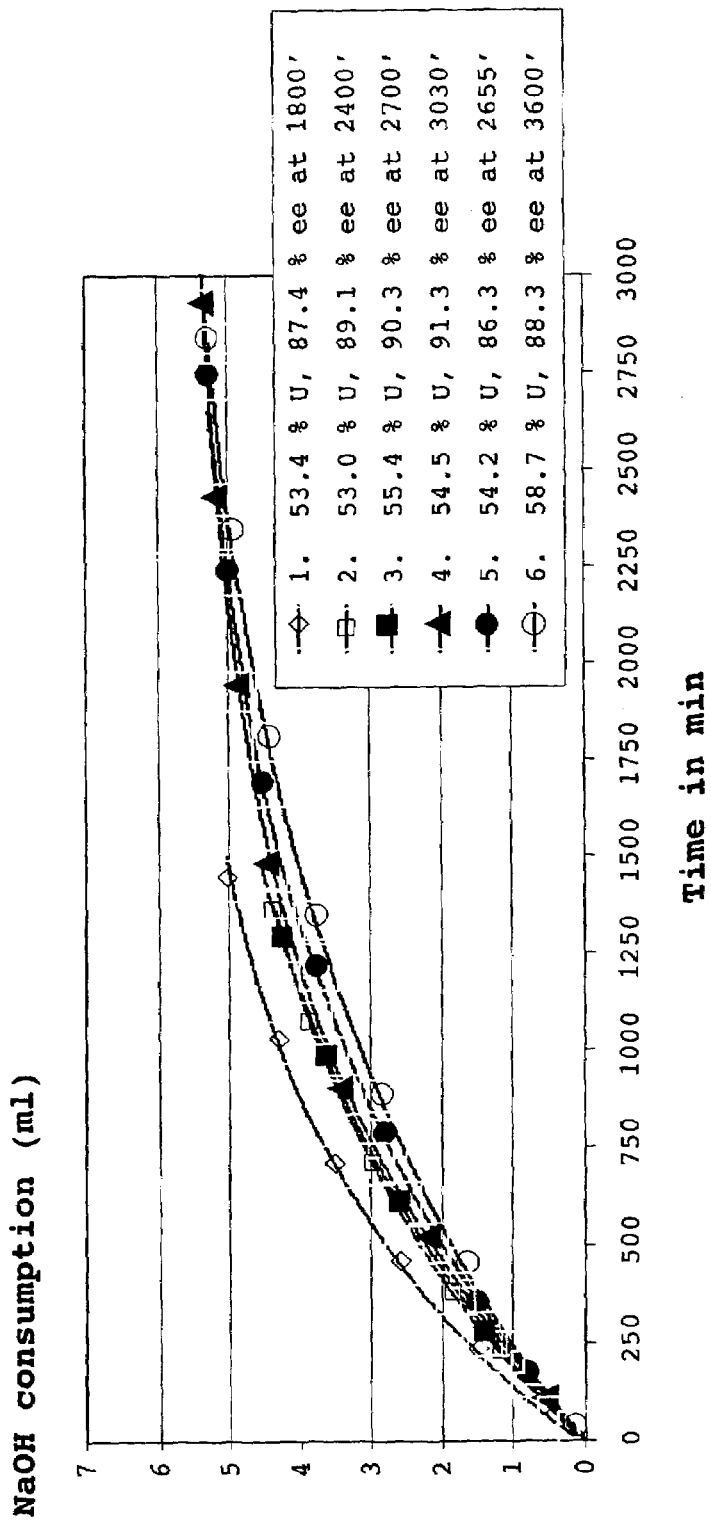

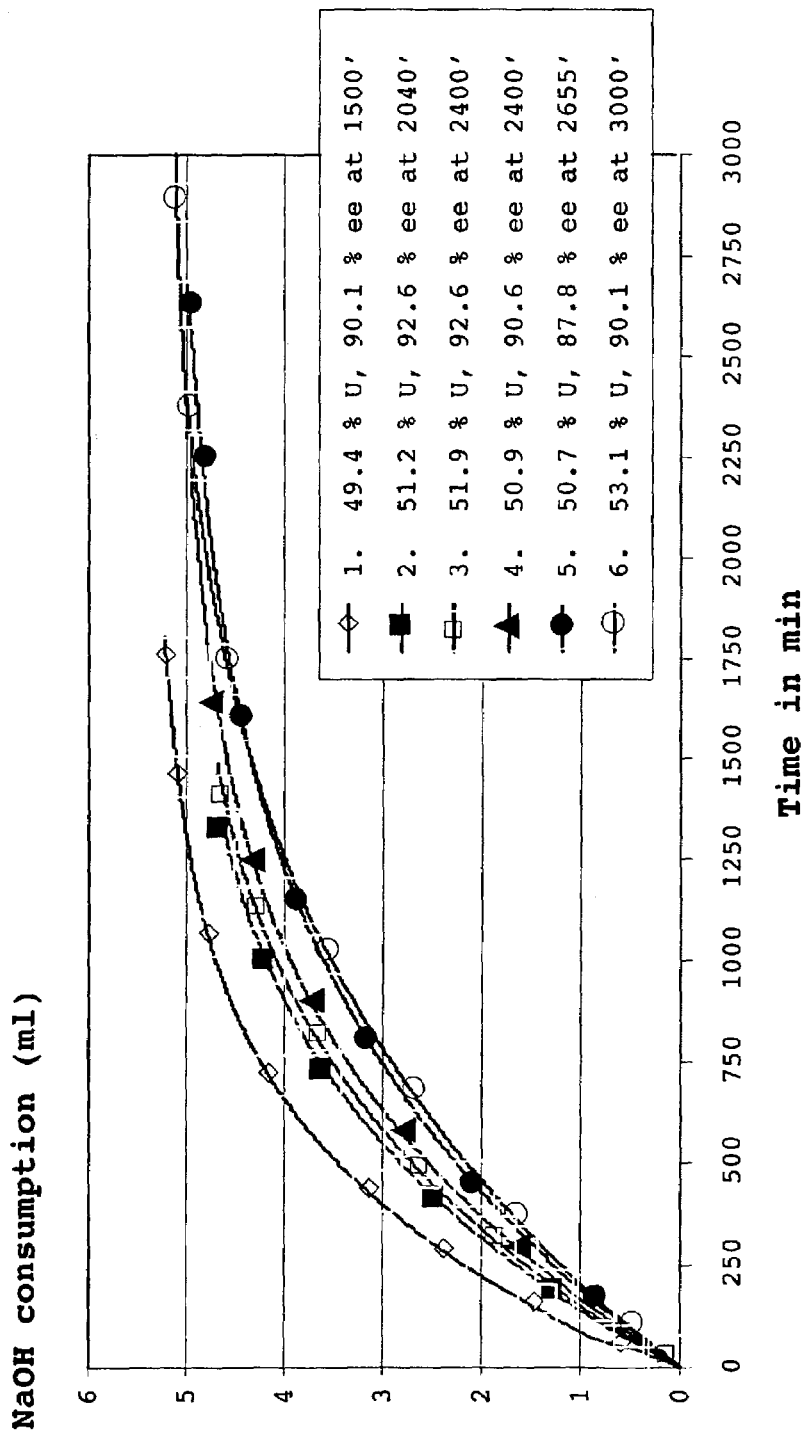
Figure 9: Useful life of L-pantolactone hydrolase immobilized on DAPIII red, 56.2 U/g, 11.9% w/v in the batch

L-PANTOLACTONE-HYDROLASE AND A METHOD FOR PRODUCING D-PANTOLACTONE

The present invention relates to proteins which have an enzymatic activity for hydrolyzing L-pantolactone. The invention further relates to nucleic acids which code for these proteins, to nucleic acid constructs, vectors, genetically modified microorganisms and to a process for preparing D-pantolactone.

D-Pantolactone is a precursor in the chemical synthesis and biosynthesis of pantothenic acid, panthenol and pantethein and derivatives thereof. These are employed as vitamin supplements in the human diet, in animal feed, in medicine, for example for wound healing, and in cosmetics, for example in hair cosmetics. Economic processes for synthesizing enantiomerically pure D-pantolactone are therefore of great importance. Besides the chemical processes which have long been carried out for preparing D-pantolactone, more recently various biotechnological processes have also been worked out. A review on pantolactone and its chemical synthesis is to be found in Ullmann's Encyclopedia of Industrial Chemistry (Vol. A27, 1996, VCH Verlagsgesellschaft mbH, 69451 Weinheim, pages 559–566).

Various synthetic strategies have been followed for the biotechnological synthesis of pantolactone.

A racemate resolution by selective hydrolysis of O-acetyl pantolactone using lipases or esterases is described by Glänzer et al. (1988, Enzyme Microb. Technol. 10, 689–690). A racemate resolution of this type is claimed in the patents DE 40 05 150 and EP-A-0 507 278. The enantiomeric purity which can be achieved in this process is insufficient for industrial use.

Degussa has described the preparation of pantolactone using the enzyme oxynitrilase starting from hydroxypivalaldehyde and hydrocyanic acid via optically pure hydroxypivalaldehyde cyanhydrin (DE 41 26 580, EP-A-0 528 256, DE 41 39 987). A 100% yield can theoretically be achieved in this reaction. The disadvantages of this reaction are the large amount of enzyme required (equimolar amounts of enzyme and substrate), and the relatively low enantiomeric purity of the product (max. 82% ee).

JP 47019745 describes the synthesis of D-pantolactone using *Arthrobacter, Brevibacterium, Bacillus* or *Corynebacterium*. In the reaction, said organisms convert racemic pantolactone into D-pantolactone by metabolizing L-pantolactone. The disadvantage of this process is that half the precursor is metabolized and thus lost.

Mitsubishi Chemical Ind. and Ube Ind. have claimed processes for preparing D-pantolactone from D,L-pantolactone (JP 6067320, JP 62294092, JP 62294096, JP 57152895). In these processes, L-pantolactone hydrolases from the yeasts *Rhodotorula, Sporidiobolus* and *Sterigmatomyces* are described. However, the current view (see Yamada & Shimizu, Ann. N.Y. Acad. Sci. 672 [1992] in Enzyme Eng. XI, Clark et al., 372–386; Chimia, 47, 1993: 5–10, JP 62187426; JP 61293384; JP 61293386; Angew. Chem. Int. Ed. Engl. 27, 1988: 622–642, Chemical Aspects of Enzyme Biotechnology, eds. T. O. Baldwin et al., Plenum Press, New York, 1990: 151–163), confirmed by our own studies, is that it is doubtful whether there is direct hydrolysis of L-pantolactone in these yeasts. Rather the reaction proceeds via ketopantolactone which is converted by ketopantoate oxidoreductases into L-pantolactone. In our own studies it was possible to detect ketopantolactone as intermediate, that is to say there is no direct hydrolysis to L-pantolactone. The disadvantage of this process is the low pantolactone concentration which can be converted in the process.

This reaction via ketopantolactone and ketopantoate oxidoreductases has also been described for bacteria (e.g. Yamada & Shimizu, see above; Shimizu et al., 1988, J. Biol. Chem. 263, 12077–12084, Kataoka et al. 1992, Eur. J. Biochem. 204, 799–806). Although corresponding processes for the enantioselective synthesis of D-pantolactone from D,L-pantolactone via ketopantolactone and ketopantoate have the advantage of a high yield (theoretically 100%, 90.5% achieved with *Rhodococcus* see below), they are uneconomic because of the cofactor requirement (NADH or NADPH), the feeding with an energy substrate (glucose), the low space-time yield and the low final concentrations (18.2–72 g/l D-pantolactone). A further disadvantage of such a process is that the two enzymes involved usually have different optima for the conversion conditions, a problem which does not arise on use of a single (hydrolytic) enzyme.

Fuji in collaboration with the Yamada research group at Kyoto University has developed a process for enzymatic racemate resolution using a fungal D-pantolactone hydrolase (JP 09308-497, JP 11056356, EP-B-0 436 730, EP-B-0 504 421, EP-A-0 794 251, WO 92/06182, WO 97/10341, U.S. Pat. No. 5,275,949, U.S. Pat. No. 5,372,940). The enzyme can be isolated, for example, from the fungi *Cylindrocarpon tonkinense, Gibberella fujikuroi* and *Fusarium oxysporum*. The D-pantolactone hydrolase is a glycosylated enzyme which consists of a 125 kDa homodimer and is $Ca^{2+}$-dependent (Ann. N.Y. Acad. Sci. 1996, 799: 650–658, Enzyme Engineering). The enzyme is inhibited by $Cd^{2+}$, $Hg^{2+}$, $Cu^{2+}$ and EDTA (U.S. Pat. No. 5,372,940). The purification of D-pantolactone hydrolase has been described by Shimizu et al. The purified enzyme shows hydrolase activity for a number of lactones, specifically for sugar lactones (Eur. J. Biochem., 209, 1992: 383–390). Its sequence shows low degrees of homology with the gluconolactonase from *Zymomonas mobilis* (28.9%), the human and rat [sic] paraoxonase (25.3%) and the strictosidin synthase from *Catharanthus roseus* (15.9%; EP-A-0 794 251, Kobayashi et al. 1998, Proc. Natl. Acad. Sci. USA, 95, 12787–12792). Kataoko et al. describe a great dependence of the enantiomeric purity obtained for the product on the conversion at different pH values (Enzym. Microbiol. Technol. 19: 307–310, 1996 and Appl. Microbiol. Biotechnol. 1995, 44: 333–338). Lower enantiomeric purities are obtained at pH values near to or above pH 7 because the spontaneous chemical hydrolysis of L-pantolactone increases at higher pH values and thus the enantiomeric purity of the product is reduced. pH 5 is stated to be the optimal pH for preparing D-pantolactone of maximum enantiomeric purity. However, the enzymatic reaction rate is considerably slowed down at this pH. In order to obtain optically pure product it is necessary to follow the extraction by a crystallization (Yamada, H. Chimia 47, 1993: 5–10).

The disadvantages of the abovementioned processes are that they frequently lead to products with only low optical purity and/or that they take place with only low space-time yields. This leads to economically unattractive processes. Thus there is still a great need for a simple, economic biotechnological process for preparing D-pantolactone which does not have the abovementioned disadvantages. It was intended that this process make it possible, starting from the existing chemical synthesis, to obtain D-pantolactone simply and in high yields and in enantiomeric purities so that no further purification of the product is necessary.

It is an object of the present invention to provide a simple, economic process for preparing D-pantolactone. We have found that this object is achieved by an isolated nucleic acid sequence which codes for a polypeptide having L-pantolactone hydrolase activity, selected from the group of:
a) a nucleic acid sequence having the sequence depicted in SEQ ID NO: 1,
b) nucleic acid sequences which, as a result of the degeneracy of the genetic code, are derived from the nucleic acid sequence depicted in SEQ ID NO: 1,
c) derivatives of the nucleic acid sequence depicted in SEQ ID NO: 1 which code for polypeptides having the amino acid sequences depicted in SEQ ID NO: 2, and have at least 50% homology at the amino acid level with a negligible reduction in the enzymatic action of the polypeptides,
d) functional equivalents of the sequences mentioned under (a) to (c).

These L-pantolactone hydrolases can be found in organisms, advantageously microorganisms such as bacteria. The enzyme or the enzymes have a high enzymatic activity for the hydrolytic conversion of L-pantolactone into L-pantoic acid.

These L-pantolactone hydrolases do not convert D-pantolactone, so that the organisms, extracts or purified enzymes, and corresponding recombinant strains or proteins, can be used to prepare enantiomerically pure D-pantolactone.

Derivatives of the nucleic acid sequence according to the invention having the sequence SEQ ID NO: 1 mean, for example, allelic variants which have at least 50% homology at the derived amino acid level, preferably at least 60% homology, particularly preferably 70%, very particularly preferably at least 80%, homology. The homology was determined by the method of either Needleman & Wunsch (J. Mol. Biol. 48, 1970: 443–453) or Smith & Waterman (Adv. Appl. Math., 2, 1981: 482–489). The homologies may advantageously be higher over some regions of the sequences. The amino acid sequence derived from SEQ ID NO: 1 is to be found in SEQ ID NO: 2. Allelic variants comprise in particular functional variants which can be obtained from the sequence depicted in SEQ ID NO: 1 by deletion, insertion or substitution of nucleotides, although there ought to be a negligible reduction in the enzymatic activity of the derived synthesized proteins. Enzymes with negligibly reduced enzymatic activity mean enzymes which have an enzymatic activity of at least 20%, preferably 50%, particularly preferably 75%, very particularly preferably 90%. The invention thus also relates to amino acid sequences which are encoded by the group of nucleic acid sequences described above. The invention advantageously relates to amino acid sequences encoded by the sequence SEQ ID NO: 1.

Functional equivalents of the sequences mentioned under (a) to (c) mean nucleic acids which code for enzymes which hydrolyze L-pantolactone to the corresponding acid and which have at least 20%, preferably 50%, particularly preferably 75%, very particularly preferably 90% of the activity of the sequence mentioned under SEQ ID NO: 2, are not inhibited by EDTA (1 mM solution) and are stable between pH 4 to [sic] 10. In addition, these functional equivalents advantageously have a pH optimum between pH 7 and 8 and a temperature optimum between 70° C. and 80° C.

Derivatives also mean homologs of SEQ ID NO: 1, for example fungal or bacterial homologs, truncated sequences, single-stranded DNA or RNA of the coding and noncoding DNA sequence. Homologs of SEQ ID NO: 1 have, at the DNA level, a homology of at least 50%, preferably of at least 60%, particularly preferably of at least 70%, very particularly preferably of at least 80%, over the whole DNA region indicated in SEQ ID NO: 1.

In addition, homologs of SEQ ID NO: 1 mean derivatives such as, for example, promoter variants. The promoters which are upstream of the stated nucleotide sequences may be modified by one or more nucleotide exchanges, by insertion(s) and/or deletion(s) without, however, impairing the functionality or activity of the promoters. The promoters may moreover have their activity increased by modification of their sequence, or be completely replaced by more effective promoters even from heterologous organisms.

Derivatives also mean variants whose nucleotide sequence in the region from −1 to −200 in front of the start codon or 0 to 1000 base pairs after the stop codon have [sic] been modified so that gene expression and/or protein expression is altered, preferably increased.

The nucleic acid sequences according to the invention can in principle be identified and isolated from all organisms. SEQ ID NO: 1 or its homologs can advantageously be isolated from fungi, yeasts or bacteria. Bacteria which may be mentioned are Gram-negative and Gram-positive bacteria. The nucleic acid(s) [the plural and singular are intended to have the same meaning for the application] according to the invention are preferably isolated by methods known to the skilled worker from Gram-negative bacteria, advantageously from α-proteobacteria, β-proteobacteria or γ-proteobacteria, particularly preferably from bacteria of the families Enterobacteriaceae, Pseudomonadaceae or Rhizobiaceae, very particularly preferably from bacteria of the genus *Agrobacterium, Pseudomonas* or *Burkholderia*. Advantageously suitable fungi which may be mentioned are the genera *Beauveria* or *Psilocybe*. Examples of advantageous yeasts are to be found in the genus *Apiotrichum*.

SEQ ID NO: 1 or its derivatives, homologs or parts of these sequences can be isolated, for example, using conventional hybridization methods or the PCR technique from other fungi or bacteria. These DNA sequences hybridize under standard conditions with the sequences according to the invention. It is advantageous to use for the hybridization short oligonucleotides of the conserved regions, for example from the active site, which can be determined in a manner known to the skilled worker by comparison with D-pantolactone hydrolase (an example of a region of this type is the so-called HTGT motif). However, it is also possible to use longer fragments of the nucleic acids according to the invention or the complete sequences for the hybridization. These standard conditions vary depending on the nucleic acid used: oligonucleotide, longer fragment or complete sequence, or depending on which type of nucleic acid, DNA or RNA, are used for the hybridization. Thus, for example, the melting temperatures for DNA:DNA hybrids are about 10° C. lower than those for DNA:RNA hybrids of the same length.

Standard conditions mean, for example, depending on the nucleic acid, temperatures between 20 and 70° C. in an aqueous buffer solution with a concentration between 0.1 to 5×SSC (1×SSC=0.15 M NaCl, 15 mM sodium citrate, pH 7.2) or additionally in the presence of 50% foramide. The hybridization conditions for DNA:RNA hybrids are advantageously 2.0×SSC and temperatures between about 20° C. to 70° C., preferably between about 50° C. to 70° C. The hybridization conditions for DNA:RNA hybrids are advantageously 2.0×SSC and temperatures between about 20° C. to 60° C., preferably between about 35° C. to 60° C. These temperatures stated for the hybridization are melting temperatures calculated by way of example for a nucleic acid with a length of about 1000 nucleotides and a G+C content of 50% in the absence of formamide. The experimental conditions for DNA hybridization are described in relevant textbooks of genetics such as, for example, Sambrook et al., "Molecular Cloning", Cold Spring Harbor Laboratory, 1989, and can be calculated by formulae known to the skilled worker, for example depending on the length of the nucleic acids, the nature of the hybrids or the G+C content. Further information of hybridization can be found by the skilled worker in the following textbook: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The nucleic acid construct according to the invention means the L-pantolactone hydrolase genes having sequence SEQ ID No: 1 and its derivatives and homologs which are functionally linked to one or more regulatory signals, advantageously to increase gene expression. These regulatory sequences are, for example, sequences to which inducers or repressors bind and thus regulate the expression of the nucleic acid. In addition to these novel regulatory sequences, it is possible for the natural regulation of these sequences still to be present in front of the actual structural genes and, where appropriate, to have been genetically modified so that the natural regulation has been switched off and the expression of the genes has been increased. However, the nucleic acid construct may also have a simpler structure, that is to say no additional regulatory signals have been inserted in front of the sequence SEQ ID No: 1 or its homologs, and the natural promoter with its regulation has not been deleted. Instead, the natural regulatory sequence is mutated so that regulation no longer takes place and gene expression is increased. It is also advantageous for the nucleic acid construct additionally to comprise one or more so-called enhancer sequences functionally linked to the promoter, which make increased expression of the nucleic acid sequence possible. Additional advantageous sequences can also be inserted at the 3' end of the DNA sequences, such as further regulatory elements or terminators. The nucleic acids according to the invention may be present in one or more copies in the construct. The construct may also comprise further markers such as antibiotic resistances or genes complementing auxotrophies, where appropriate, for selecting for the construct.

DESCRIPTION OF THE DRAWINGS

FIG. 1a is a graphical representation of the temperature optimum for L-pantalactone hydrolase from *Burkholderia caryophylli* Lu681.

FIG. 1b is a graphical representation of the temperature optimum for L-pantalactone hydrolase from *Agrobacterium radiobacter* Lu53511.

FIG. 2a is a graphical representation of the pH optimum for L-pantalactone hydrolase from *Burkholderia caryophylli* Lu681.

FIG. 2b is a graphical representation of the pH optimum for L-pantalactone hydrolase from *Agrobacterium radiobacter* Lu53511.

FIG. 3 is a restriction map of pKS+681.

FIG. 4 is a restriction map of pKK681.

FIG. 5 is a restriction map of pDHE681.

FIG. 7 is a graphical representation of the useful life of Lu9981 homogenate.

FIG. 8 is a graphical representation of the useful life of L-pantolactone hydrolase immobilized on Engergit C, 80.8 U/g. 8.6% w/v in the batch.

FIG. 9 is a graphical representation of the useful life of L-pantolactone hydrolase immobilized ib DAPIII red, 56.2 U/g. 11.9% w/v in the batch.

Figure 6:
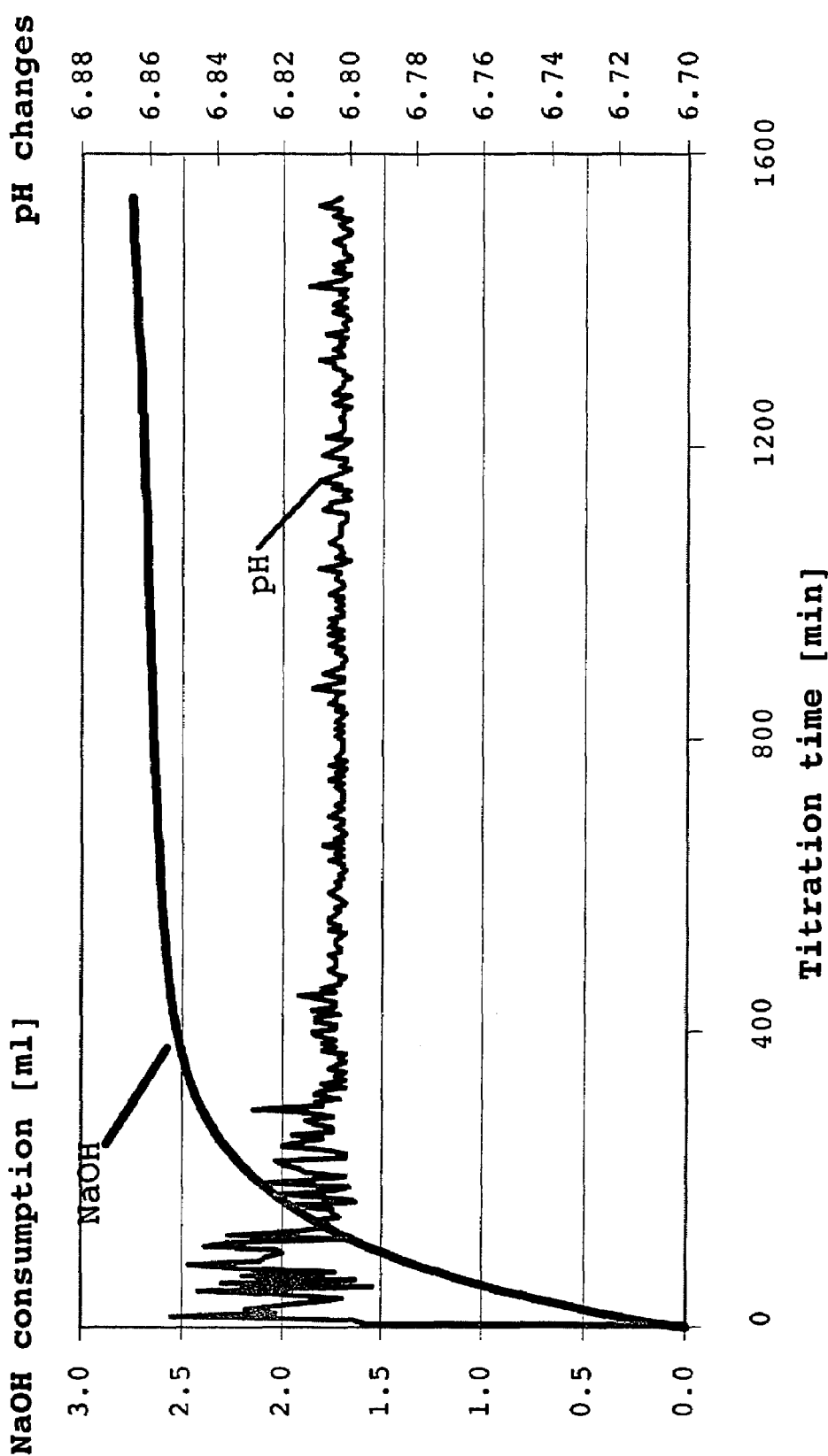
FIG. 6 is a graphical illustration of the relatively constant pH during NaOH consumption over a period of time.

Advantageous regulatory sequences for the process according to the invention are, for example, present in promoters such as aphII (Tn5), trc, cos, tac, trp, lacPAI, rha, tet, trp-tet, lpp, lac, lpp-lac, lacI$^q$, T7, T5, T3, gal, trc, ara, SP6, $\lambda P_R$ or $\lambda$-$P_L$ promoter, which are advantageously used in Gram-negative bacteria. Further advantageous regulatory sequences are, for example, present in the Gram-positive promoters such as in the constitutive or inducible *streptomyces* promoters aphI, ermE, melC, tipA, mcrAB, gylCAB, veg, SPO1, amy and SPO2, in the yeast or fungal promoters AOX1, GAL1, ADC1, MFα, AC, P-60, CYC1, GAPDH, TEF, rp28, ADH. In this connection, the promoters of pyruvate decarboxylase and methanol oxidase from, for example, *Hansenula* are also advantageous. It is also possible to use artificial promoters for the regulation.

For expression, the nucleic acid construct is inserted into a host organism, advantageously into a vector, such as, for example, a plasmid, a phage or other DNA, which makes optimal expression of the genes in the host possible. These vectors represent a further embodiment of the invention. Examples of suitable plasmids are in *E. coli* pBluescript, PBAD, pQE (His tag System), pICIC223-3, pLG338, pACYC184, pBR322, pUC18, pGEM7Z, pKK223-3, pUC19, pKC30, pRep4, pHS1, pHS2, pPLc236, pMBL24, pLG200, pUR290, pIN-III$^{113}$-B1, λgtl1 or pBdCI or broad host-range plasmids such as pBBR1MCS or pRK293, in *streptomyces* and other actinomycetes pIJ101, pIJ364, pMVS301, pIJ702 or pIJ361, in *Bacillus* pUBI110, pC194 or pBD214, in *Corynebacterium* pSA77 or pAJ667, in fungi pALS1, pIL2 or pBB116, in yeasts 21 µM[sic], pAG-1, YEp6, YEp13 or pEMBLYe23 or in plants pLGV23, pGHlac+, pBIN19, pAK2004 or pDH51. Said plasmids represent a small selection of the possible plasmids. Further plasmids are well known to the skilled worker and can be found, for example, in the book Cloning Vectors (Eds. Pouwels P. H. et al. Elsevier, Amsterdam-New York-Oxford, 1985, ISBN 0 444 904018).

The nucleic acid construct advantageously contains, for expression of the other genes present, in addition 3' and/or 5' terminal regulatory sequences to increase expression, these being selected for optimal expression depending on the selected host organism and gene or genes.

These regulatory sequences are intended to make specific expression of the genes and of the protein expression possible. This may mean, for example depending on the host organism, that the gene is expressed or overexpressed only after induction, or that it is expressed and/or overexpressed immediately.

The regulatory sequences or factors may for this purpose preferably have a beneficial effect on expression of the introduced genes, and thus increase it. Thus, an enhancement of the regulatory elements can advantageously take place at the level of transcription, by using strong transcription signals such as promoters and/or enhancers. However, it is also possible to enhance translation by, for example, improving the stability of the mRNA.

In a further embodiment of the vector, it is also possible for the vector comprising the nucleic acid construct according to the invention or the nucleic acid according to the invention advantageously to be introduced in the form of a linear DNA into the microorganisms, and be integrated by heterologous or homologous recombination into the genome of the host organism. This linear DNA may consist of a linearized vector such as a plasmid or only of the nucleic acid construct or the nucleic acid according to the invention.

The invention further relates to an L-pantolactone hydrolase having the following properties:
a) conversion of L-pantolactone into the corresponding acid,
b) pH stability: L-pantolactone hydrolase is stable in a pH range from 4 to 10
c) pH optimum: 7.2 to 7.6
d) temperature optimum: about 70° C. to 75° C.
e) no inhibition of the activity by EDTA This L-pantolactone hydrolase can be used in the process according to the invention as free or immobilized enzyme.

For optimal expression of heterologous genes in organisms it is advantageous to modify the nucleic acid sequences in accordance with the specific codon usage of the organism. The codon usage can easily be established on the basis of computer analyses of other, known genes of the relevant organism.

Expression of the genes according to the invention and of the proteins encoded by these genes in a host organism ordinarily entails a stress for these organisms. Simultaneous expression of these genes in the presence of at least one gene which codes for a so-called stress protein or in the presence of a combination of these genes makes it possible for the nucleic acids according to the invention advantageously to be expressed in the host organisms according to the invention. Stress proteins, also called heat shock proteins (=HSP) or molecular chaperones, are among the proteins which have been conserved best during evolution, both in prokaryotes and in eukaryotes, and are to be found universally in all organisms. They are classified according to the molecular weight in kilodalton, e.g. HSP60, 70, 90 etc. These stress proteins derive their name from their property of being inducible by stress conditions such as the glucose level being too low, heat shock, alcohol, UV light, oxidative reagents etc.

Many stress proteins and related proteins which are formed constitutively are essential for the correct folding, association, stabilization and transport of proteins. Coexpression of the proteins according to the invention in the presence of at least one stress protein makes it possible advantageously to express the nucleic acids according to the invention. It is possible in this way advantageously to prevent any aggregation of the hydrolyase proteins occurring. This entails the stress proteins binding to hydrophobic parts of the proteins and thus preventing incorrect folding of the proteins and facilitating correct folding. Proteins which have already aggregated or been denatured are dissociated again and correctly folded. When these stress proteins carry out their function they frequently cooperate with other proteins, called helper proteins (=cohort proteins) and thus there is use of the term chaperone machines, which have the advantageous effect on expression of the genes according to the invention (Frydaman [sic] et al., Nature, 370, 1994: 111–117). The effect of these chaperone machines may take place with ATP consumption (="main chaperone machines") or without ATP consumption (="junior chaperones"). Examples of advantageous chaperones or heat shock proteins are the eukaryotic genes HSP17.5, HSP22, HSP 25, HSP27, HSP60, HSP70, HSP90, TRiC, UBI1, 2, 3, 4 or their prokaryotic homologs such as HtpG, DnaK, DnaJ, GroES, GroEL, HtrC, ClpB, GrpE etc. Preferred chaperones are GroES, GroEL, HtpG, DnaK, DnaJ, HSP70 or HSP27.

The nucleic acids according to the invention are advantageously expressed in the presence of at least one stress protein, in which case the genes can be under the joint control of one promoter or be read from separate promoters. Accordingly, their expression can be induced by adding one or more inducer substances simultaneously or at separate times. The nucleic acids may be present on one vector or on separate vectors. It is also possible to modify the stress proteins of the host organism by genetic manipulation so that they are overexpressed.

Alternative methods for increasing the native enzyme content may also be advantageous, such as cultivation of the microorganisms which synthesize the protein according to the invention at low temperatures, or renaturation by use of high pressures (advantageously 1 to 2 kbar) on suspensions of the protein according to the invention (with or without the addition of denaturing agents, for example guanidine hydrochloride).

Suitable recombinant host organisms for the nucleic acid according to the invention or the nucleic acid construct are in principle all prokaryotic or eukaryotic organisms. The host organisms advantageously used are microorganisms such as bacteria, fungi or yeasts. Gram-positive or Gram-negative bacteria are advantageous, preferably bacteria from the families Enterobacteriaceae, Pseudomonadaceae, Rhizobiaceae, Streptomycetaceae or Nocardiaceae, yeasts such as *Pichia*, *Saccharomyces* or *Hansenula* or fungi such as *Beauveria* or *Psilocybe*, particularly preferably bacteria from the genera *Escherichia*, *Pseudomonas*, *Streptomyces*, *Nocardia*, *Burkholderia*, *Salmonella*, *Agrobacterium* or *Rhodococcus*. The genus and species *Escherichia coli* is very particularly preferred. Further advantageous bacteria are moreover to be found in the group of $\alpha$-proteobacteria, $\beta$-proteobacteria or $\gamma$-proteobacteria.

The host organism or the host organisms according to the invention preferably comprise in this connection at least one of the nucleic acid sequences, nucleic acid constructs or vectors described in this invention, which code for L-pantolactone hydrolases.

The organisms used in the process according to the invention are grown or cultivated in the manner known to the skilled worker depending on the host organism. Microorganisms are ordinarily grown in a liquid medium which contains a carbon source, usually in the form of sugars, a nitrogen source, usually in the form of organic nitrogen sources such as yeast extract or salts such as ammonium sulfate, trace elements such as iron, manganese, magnesium salts and, where appropriate, vitamins, at temperatures between 0° C. and 100° C., preferably between 10° C. to [sic] 60° C., aerating with oxygen. It is moreover possible to maintain the pH of the nutrient liquid at a fixed value, that is to say regulate it during cultivation, or not. Cultivation can take place batchwise, semibatchwise or continuously. Nutrients can be introduced at the start of the fermentation or be replenished semicontinuously or continuously. The same applies to inducers such as, for example, isopropy [sic] thiogalactoside, (IPTG), lactose, arabinose, rhamnose and antibiotics and/or temperature shifts which bring about the expression of the gene according to the invention depending on the promoter used. The racemic pantolactone can be added directly to the cultivation or, advantageously, after the cultivation. The enzymes can be isolated from the organisms by the process described in the examples or be used as crude extract for the reaction.

The host organisms advantageously contain 0.5 U/g DBM (=dry biomass) L-pantolactone hydrolase activity, preferably 4 U/g DBM, particularly preferably 20 to 150 U/g DBM, very particularly preferably 40 to 60 U/g DBM.

The process according to the invention is advantageously carried out at a temperature between 0° C. to [sic] 95° C., preferably between 10° C. to [sic] 85° C., particularly preferably between 15° C. to [sic] 75° C.

The pH in the process according to the invention is advantageously kept between pH 4 and 12, preferably between pH 6 and 9, particularly preferably between pH 6 and 8, very particularly preferably between pH 6.5 and 7.5.

Racemic pantolactone in the process according to the invention means pantolactone which consists of a 50:50 mixture of the two enantiomers or of any other mixture with enrichment of one of the two enantiomers in the mixture.

Enantiomerically pure or chiral pantolactone (D or L enantiomer) means in the process according to the invention enantiomers which show enrichment of one enantiomer. The process preferably achieves enantiomeric purities of at least 70% ee, preferably of at least 80% ee, particularly preferably of at least 90% ee, very particularly preferably at least 98% ee.

It is possible to use for the process according to the invention growing cells which comprise the nucleic acids, nucleic acid constructs or vectors according to the invention. It is also possible to use resting or disrupted cells. Disrupted cells mean, for example, cells which have been made permeable by treatment with, for example, solvents, or cells which have been ruptured by an enzyme treatment, by a mechanical treatment (for example French press or ultrasound) or by another method. The crude extracts obtained in this way are advantageously suitable for the process according to the invention. Purified or partially purified enzymes can also be used for the process. Likewise suitable are immobilized microorganisms or enzymes which can advantageously be used in the reaction.

If free organisms or enzymes are used for the process according to the invention, these are expediently removed, for example by filtration or centrifugation, before the extraction. It is advantageous that this is unnecessary on use of immobilized organisms or enzymes, but it may still take place.

The D-pantolactone prepared in the process according to the invention can advantageously be isolated from the aqueous reaction solution by extraction or crystallization or, advantageously, by extraction and crystallization. This is done by extracting the aqueous reaction solution with an organic solvent. The extraction can be repeated several times to increase the yield. The solution is advantageously cooled to about 0° C. to 10° C. before the extraction. The aqueous solution is advantageously neutralized to about pH 6.0 to pH 7.0, before the cooling or thereafter, in order to convert the free acid into the salt so that the former cannot be extracted under the reaction conditions. A base used for the neutralization is, for example, bicarbonate or another one such as NaOH or KOH. The organic solvents which can be used in principle are all solvents which show a phase boundary with water, where appropriate after addition of salts, and into which the lactone can migrate from the aqueous phase. Advantageous solvents are solvents which take up only a small amount of water so that only a small amount of acid migrates into the solvent, such as toluene, methylene chloride, butyl acetate, diisopropyl ether, benzene, methyl tertiary-butyl ether, methyl isobutyl ketone, diethyl ketone or ethyl acetate.

After concentration of the organic phase, the products can usually be obtained in good chemical purities, that is to say greater than 90% chemical purity. After extraction, the organic phase with the product can, however, also be only partly concentrated, and the product can be crystallized out. This is done advantageously by cooling the solution to a temperature of from 0° C. to 10° C. Crystallization is also possible directly from the organic solution or from an aqueous solution. The crystallized product can be taken up again in the same or in a different solvent for recrystallization and be crystallized again. It is possible by the subsequent advantageous crystallization at least once to increase the enantiomeric purity of the product further if necessary. However, it is possible and advantageous for the resulting D-pantolactone to be used directly as organic solution without crystallization.

The L enantiomer remaining in aqueous solution can be lactonized by acidification, for example with sulfuric acid, and then be extracted as described above. The solution is advantageously heated for the lactonization. The L-lactone obtained can, after the solvent has been stripped off, be racemized in the melt with catalytic amounts (about 1 to 5% mol %) of a base such as NaOH, Na pantoate or Na methoxide, and be recycled. The advantageous racemization and recycling of the unwanted enantiomer makes it possible to achieve a theoretical yield of 98% in the process according to the invention.

With the types of work up mentioned, the product of the process according to the invention can be isolated in yields of from 60 to 100%, preferably from 80 to 100%, particularly preferably from 90 to 100%, based on the racemic pantolactone employed for the reaction. The isolated product is distinguished by a high chemical purity of >90%, preferably >95%, particularly preferably >98%. In addition, the product have a high enantiomeric purity, which can advantageously be further increased where necessary by the crystallization.

The process according to the invention can be carried out batchwise, semibatchwise or continuously.

The products obtained in this way are suitable as starting material for the synthesis of panthenol, pantethein and derivatives thereof. These substances and the enantiomerically pure pantolactone obtained can be used in combination with one another or alone for producing drugs, foodstuffs, animal feeds or cosmetics.

The following examples illustrate the invention.

EXAMPLES

1. L-Pantolactone hydrolysis with *Burkholderia caryophylli* Lu681

*Burkholderia caryophylli* Lu681 (or others of the strains indicated in Table 1a, 1b) were grown in 25 ml of complex medium (for example HFP=1% peptone, 1% tryptone, 0.5% yeast extract, 0.3% NaCl) for 1 to 3 days, harvested, washed and resuspended in buffer (5 ml of 50 mM Tris/HCl pH 7.0) and incubated with 50 mM D,L-pantolactone at 30° C. for 3 h. After removal of these cells, the concentrations of D,L-pantolactone, D,L-, D- and L-pantoic acid were determined by GC or HPLC analysis (Tab. 1a). Alternatively, the conversion was carried out overnight titrating with 4 M NaOH (4 ml of cell suspension, 50 mM D,L-pantolactone, 50 mM Tris/HCl pH 7.0 ad 20 ml distilled water; Tab. 1b). All the strains in Table 1 hydrolyzed the racemic pantolactone to L-pantoic acid. The ee at high conversion (>45%) and thus the enantioselectivity E of the enzyme was determined as described by Straathof and Jongejan, Enzyme & Microbiol. Technology 21: 559–571, 1997.

2. Verification of the hydrolytic activity

Burkholderia caryophylli Lu681 (or other strains from Tab. 1) were grown in 25 ml of complex medium (for example HFP=1% peptone, 1% tryptone, 0.5% yeast extract, 0.3% NaCL) for 1 to 3 days, harvested, washed in Tris-HCl buffer (50 mM, pH 7.0) and resuspended (5 ml of 50 mM Tris/HCl, pH 7.0) and incubated with 50 mM ketopantolactone at 30° C. for 3 h. After removal of the cells, the concentrations of ketopantolactone, ketopantoic acid, D,L-pantolactone, D,L-, D-, and L-pantoic acid were determined by HPLC analysis (Tab. 1a). All the listed strains apart from Beauveria amorpha Lu7953 were able to reduce to pantoic acid the ketopantoic acid resulting from spontaneous hydrolysis of ketopantolactone. Since, however, D-pantoic acid was formed with all the strains instead of the L-pantoic acid described in Example 1, the conversion of pantolactone to L-pantoic acid cannot be produced by an oxidation-reduction process (via ketopantolactone and ketopantoic acid). No dependence of the L-pantolactone hydrolysis on cofactors was found in the dialyzed crude extract from Lu681 or Lu5351 and on use of the purified enzymes from Lu681 and Lu5351 either. The enzymatic activity can thus be attributed to a hydrolytic enzyme.

3. Production of D-pantolactone by hydrolysis with various wild-type strains a. Burkholderia caryophylli Lu681

Burkholderia caryophylli Lu681 was grown in 200 ml of complex medium (for example GYP=1% D-glucose, 0.5% polypeptone, 0.5% yeast extract) (OD600=6.7, DBM=2.97 g/l), harvested and washed. 10 ml of the 10-fold concentrated suspension were incubated with 50 mM D,L-pantolactone in 50 mM Tris/HCl pH 7.0 (batch volume 20 ml) at 30° C. titrating with 4 M NaOH to pH 7.0. The conversion c and the ee were determined after 3 h and 19.5 h by HPLC analysis (3 h: c=45%, ee=95%; 19.5 h: c=59%, ee=89% for L-pantoic acid). The latter corresponds to D-pantolactone with ee values of 73% and 100% respectively.

b. Agrobacterium radiobacter Lu5351

Agrobacterium radiobacter Lu5351 was grown in 200 ml of complex medium (for example HFP=1% peptone, 1% tryptone, 0.5% yeast extract, 0.3% NaCl) (OD600=11.5, DBM=2.90 g/l), harvested and washed. 10 ml of the 10-fold concentrated suspension were incubated with 50 mM D,L-pantolactone in 50 mM Tris/HCl pH 7.0 (batch volume 20 ml) at 30° C. titrating with 4 M NaOH to pH 7.0.

The conversion c and the ee were determined after 3 h and 19.4 h by HPLC analysis (3 h: c=20%, ee=93%; 19.4 h: c=53%, ee=94% for L-pantoic acid). The latter corresponds to D-pantolactone with ee values of 21% and 100% respectively.

c. Pseudomonas diminuta Lu683

Pseudomonas diminuta Lu683 was grown in 200 ml of complex medium (for example GYP=1% D-glucose, 0.5% polypeptone, 0.5% yeast extract) (OD600=7.3, DBM=3.78 g/l), harvested and washed. 10 ml of the 10-fold concentrated suspension were incubated with 50 mM D,L-pantolactone in 50 mM Tris/HCl pH 7.0 (batch volume 20 ml) at 30° C. titrating with 4 M NaOH to pH 7.0. The conversion c and the ee were determined after 3 h and 19.3 h by HPLC analysis (3 h: c=48%, ee=97%; 19.4 h: c=69%, ee=79% for L-pantoic acid). The latter corresponds to D-pantolactone with ee values of 82% and 100% respectively.

d. Apiotrichum humicola Lu3215

Apiotrichum humicola Lu3215 was grown in 200 ml of complex medium (for example HFP=1% peptone, 1% tryptone, 0.5% yeast extract, 0.3% NaCl) (OD600=18.5, DBM=7.34 g/l), harvested and washed. 10 ml of the 10-fold concentrated suspension were incubated with 50 mM D,L-pantolactone in 50 mM Tris/HCl pH 7.0 (batch volume 20 ml) at 30° C. titrating with 4 M NaOH to pH 7.0. The conversion c and the ee were determined after 3 h and 19.4 h by HPLC analysis (3 h: c=55%, ee=79% for L-pantoic acid). The latter corresponds to D-pantolactone with ee values of 84%.

4. Isolation of L-pantolactone hydrolase from Burkholderia caryophylli Lu681

Burkholderia caryophylli Lu681 was grown in 14 l of complex medium (HFP=1% peptone, 1% tryptone, 0.5% yeast extract, 0.3% NaCl) until OD600=10 (3 g/l DBM), harvested and disrupted, and the L-pantolactone hydrolase (about 200 U) was purified from the crude extract. This was done by first resuspending the cells (1128 g wet weight) in the buffer (1.8 l, 20 mM Tris/HCl, pH 7.4) by a treatment with an Ultra-Turrax shaft. Final volume 3 l. Coarse particles were then removed from this solution through a bed of glass beads (0.1 to 0.2 mm, 200 ml) on a glass suction funnel. This cell suspension (3.2 l) was homogenized twice in a Z04 microfluidizer at 1500 bar. The apparatus was rinsed with 500 ml of buffer. The combined volumes (4 l) were subjected to a first precipitation with 200 ml of a 1 M manganese chloride solution (final concentration 50 mM). The pH was kept at pH 7.0 by addition of sodium hydroxide solution. The precipitate was centrifuged down at 6000 rpm for 30 minutes. The supernatant (3.1 l) was mixed with 200 ml of a 0.2 M EDTA solution (pH 7.5). The addition resulted in the pH falling to 5.0. A precipitate formed and was again centrifuged down at 6000 rpm (Sorvall, 20 minutes). The supernatant (3.4 l) was back-titrated to pH 7.0.

Subsequently 989 g of ammonium sulfate (corresponding to a 50% saturation) were added and stirred for 10 minutes. The turbidity was centrifuged down at 6000 rpm for 20 minutes. The resulting supernatant (3.7 l) was divided: 1.2 l were employed in a phenyl-Sepharose chromatography.

The phenyl-Sepharose column (Pharmacia, diameter 5 cm, height 25 cm, volume 490 ml) was washed with 1 l of buffer A (20 mM sodium phosphate buffer, pH 7.4, 40% ammonium sulfate) and eluted in a gradient with buffer B (20 mM sodium phosphate buffer, pH 7.4). At a flow rate of 10 ml/min, 100% buffer B were reached after 120 minutes and were maintained for 40 minutes. Active fractions were collected and combined (250 ml).

After dilution to <7 mS/cm, these 3 l were purified by chromatography on Q-Sepharose (diameter 5 cm, height 25 cm, 430 ml, Fast Flow, Pharmacia). The column was washed (10 ml/min) with 1 l of buffer A (20 mM sodium phosphate buffer pH 7.4 [lacuna]. The gradient with buffer B (buffer A with 1 M NaCl) was brought to linear 100% B in 120 minutes and maintained linear at 100% for a further 40 minutes. The active fractions were collected and combined (118 ml). This volume was concentrated (10 kD Omega membrane) and dialyzed against 5 l 10 mM Tris/HCl pH 7.0; final volume 21 ml. 6 ml of this volume were loaded onto a Waters Q HR8. The column had previously been equilibrated with buffer A (20 mM Mes, pH 6.0) and then developed with a gradient (1% per minute) to buffer B (as buffer A with 0.5 M NaCl). Active fractions were combined (3.7 ml) and dialyzed twice against 2 l of 10 mM Tris/HCl pH 7.0. The dialyzate became turbid and was therefore centrifuged (4 ml).

This material was then separated by chromatography on Mono P (Pharmacia, diameter 0.5 cm, volume 5 ml). The Mono-P fractions were concentrated in 0.2 ml portions by an acetone precipitation at −20 degrees Celsius.

The pellets were then taken up in 0.005 ml of SDS sample buffer without DTT and loaded onto an SDS gel (Tris/glycine gel 12%, from Novex, about 2.5 h, 125 V, 50 mA, Laemmli, U.K., 1970, Nature, 227: 680–685). The L-pantolactone hydrolase was identified after the separation by an activity stain and was cut out. This was done by briefly agitating the gel in TBS buffer (=50 mM Tris, 100 mM NaCl, pH 7.4) and then preincubating with 50 ml of TBS+50 ml of α-naphthyl acetate solution (Sigma N-8505, 0.4 g/l in 10% acetone) for 10 min. Then 50 ml of Fast Red TR solution (Sigma F-8764, 1 g/l) were added and the gel was further agitated at RT (=about 23° C.). The L-pantolactone hydrolase was identifiable as a reddish brown band with an apparent molecular weight of about 36 kDa, The protein in the pieces of gel which had been cut out was digested with trypsin, and the peptides were sequenced. The remaining gel was stained with Coomassie Blue. Two peptide sequences (SEQ ID NO: 3 and 4) were obtained.

5. Isolation of L-pantolactone hydrolase from *Agrobacterium radiobacter* Lu5351

*Agrobacterium* radiobacter Lu5351 was grown in 14 l of complex medium (e.g. HFP=1% peptone, 1% tryptone, 0.5% yeast extract, 0.3% NaCl) until OD600=10 (3 g/l DBM), harvested and disrupted, and the L-pantolactone hydrolase (about 60 U) was purified from the crude extract (Tab. 2). This was done by first resuspending the cells (400 g wet weight) of *Agrobacterium radiobacter* (Lu 5351) in the buffer (1.8 l, 20 mM Tris/HCl, pH 7.4) by a treatment with an Ultra-Turrax shaft (final volume 2.2 l). Coarse particles were then removed from this solution through a bed of glass beads (0.1 to 0.2 mm, 200 ml) on a glass suction funnel. This cell suspension was homogenized twice in a Z04 microfluidizer at 1500 bar. The apparatus was rinsed with 500 ml of buffer. The combined volumes (2.7 l) were subjected to a first precipitation with 135 ml of a 1M manganese chloride solution (final concentration 50 mM). The pH was kept at pH 7.0 by addition of sodium hydroxide solution, and the precipitate was centrifuged down at 6000 rpm for 30 minutes. The supernatant (2.6 l) was mixed with 575 ml of a 0.2 M EDTA solution and the pH was rechecked. 711 g of ammonium sulfate (corresponding to 40% saturation) were added to this 3.15 l and stirred for 10 minutes. The turbidity was centrifuged down at 6000 rpm for 30 min. The resulting supernatant (3.3 l) was employed in a phenyl-Sepharose chromatography.

The phenyl-Sepharose column (Pharmacia, diameter 5 cm, height 25 cm, volume 490 ml) was washed with 1 l of buffer A (20 mM sodium phosphate buffer, pH 7.4, 40% ammonium sulfate) and eluted in a gradient with buffer B (20 mM sodium phosphate buffer, pH 7.4). At a flow rate of 10 ml/min, 100% B were reached after 120 minutes and were maintained for 40 minutes. Active fractions were collected and combined (350 ml, 20.9 mS).

After dilution to 7 mS/cm (3.1 l final volume), a chromatography on Q-Sepharose (diameter 5 cm, height 25 cm, 430 ml, Fast Flow, Pharmacia) was carried out. The column was washed (10 ml/min) with 1 l of buffer A (20 mM sodium phosphate buffer pH 7.4 [lacuna]. The gradient with buffer B (buffer A with 1 M NaCl) was brought to 100% B in 120 minutes and maintained at 100% for a further 40 minutes. The active fractions were collected and combined (134 ml). This volume was concentrated (10 kD Omega membrane) and dialyzed against 3 l 10 mM Tris/HCl pH 7.0; (final volume 19 ml). 6 ml of this volume were loaded onto a Waters Q HR8. The column had previously been equilibrated with buffer A (20 mM Mes, pH 6.0) and developed with a gradient (1% per minute) to buffer B (as buffer A with 0.5 M NaCl). Active fractions were combined (12.5 ml) and dialyzed twice against 5 l of 10 mM sodium acetate buffer pH 5.0. The dialyzate became turbid and was therefore centrifuged.

The supernatant was then separated by chromatography on Mono P (Pharmacia, diameter 0.5 cm, volume 5 ml).

The Mono-P fractions were concentrated in 0.2 ml portions by an acetone precipitation at −20 degrees Celsius. The pellets were then taken up in 0.005 ml of SDS sample buffer without DTT and loaded onto an SDS gel. The L-pantolactone hydrolase was identified after the separation by an activity stain (see Example 4) and was cut out. It was identifiable as a reddish brown band with an apparent molecular weight of 36 kDa. The protein in the pieces of gel which had been cut out was digested with trypsin, and the peptides were sequenced. The remaining gel was stained with Coomassie Blue. Two peptide sequences (SEQ ID NO: 5 and 6) were obtained. Sequencing of SEQ ID NO: 5 revealed that the first amino acid in the sequence was unclear. The tyrosine represented in position 1 may also be a leucine [lacuna] the sequence was ambiguous here.

6. Substrate specificity of the purified L-pantolactone hydrolases from Lu681 and Lu5351

0.1 U/ml of a phenyl-Sepharose peak fraction of the purified enzymes from Lu681 or Lu5351 was incubated in 150 mM Pipes pH 6.8 with various esters and lactones. Samples were taken after 0, 1 and 20 h, the reaction was stopped by centrifugation through a 10 kDa filter membrane, and the concentration of the substrate and of the corresponding acid was determined by HPLC analysis. The activity is indicated in Tables 3a and 3b compared with the activity with L-pantolactone.

For the lipase substrate 1,2-O-dilauryl-rac-glycero-3-glutaric acid resorufin ester, an optical assay in a microtiter plate (Boehringer Mannheim, modified) was carried out for the Lu681 enzyme. 60 to 482 U/l enzyme were incubated in 45 mM $KH_2PO_4$ pH 6.8 with 0.18 g/l resorufin ester (2 g/l in dioxane+2% SDS+10% $H_2O$) at room temperature. The extinction E was measured at 572 nm after 2 min and 82 min. Tab. 3c shows the difference in extinction and the lipase activity calculated therefrom, which amounts to about 0.05% of the L-pantolactone hydrolase activity.

7. Inhibition and activation of the purified L-pantolactone hydrolases from Lu681 and Lu5351

0.1 U/ml of a phenyl-Sepharose peak fraction of the purified proteins from Lu681 or Lu5351 was preincubated with various effector substances in 150 mM Pipes (pH 7.0) for 5 min. The assay was started by adding 150 mM L-pantolactone (1 h at 30° C.) and stopped by centrifugation through a 10 kDa filter membrane. The concentrations of D,L-, D-, and L-pantoic acid were then determined by HPLC analysis. Tables 4a and 4b show the activity compared with the sample without added effector substance. Overall, the purified enzymes from Lu681 and Lu5351 are insensitive (>85% residual activity) to chelating substances, SH reagents, protease inhibitors, detergents (exception: Lu5351 with 74% residual activity in 1% SDS) and various cations.

A significant activation (+20%) is to be found at the most with $HgCl_2$ (133/170%). In addition, a competitive inhibition by D-pantolactone was detected for the recombinant 681 lactonase (*E. coli* cells, see Ex 8 et seq.)

8. Genbank+Screening: cloning of the L-pantolactone hydrolase from *Burkholderia caryophylli* Lu681

Genomic DNA from *Burkholderia caryophylli* Lu681 was isolated (Qiagen, Hilden), digested with EcoRI and ligated into a pBluescriptKS+-vector which had been cut with EcoRI and dephosphorylated (Maniatis, T., Molecular Cloning: A laboratory manual, 1989). The ligation mixture was transformed into *E. coli* XL1 Blue in accordance with Stratagene's instructions (La Jolla, Calif.). The transformants were plated out on LB plates with ampicillin (100 µg/ml), IPTG (=isopropyl β-thiogalactoside, 0.2 mM) and X-Gal (80 mg/l) and incubated at 30 or 37° C. overnight. The white colonies were picked onto LB plates with ampicillin (100 µg/ml), IPTG (0.2 mM) and X-Gal (80 mg/l) and again incubated overnight. A copy of this master plate was then made by filter replication using sterile nitrocellulose filters on LB-ampicillin (100 mg/ml)-IPTG plates. After incubation overnight on this plate (see above) the filter underwent an activity assay with 150 mM L-pantolactone, 0.1% nitrazine yellow and 10 mM Tris/HCL pH 7.0 (3 h-overnight, 30° C.). A clone with a yellow color (XL1 Blue pKS+681) was isolated.

9. Restriction mapping and sequencing of the EcoRI insert from *E. coli* XL1Blue pKS+681

The plasmid DNA was isolated in accordance with the instructions of Qiagen (Hilden) from *E. coli* XL1Blue pKS+681 and was cut with the restriction enzymes EcoRI, BamHI, PstI and HindIII singly and by double digestion. The fragmented DNA was analyzed by agarose gel electrophoresis in a 0.8% agarose gel. The fragment sizes obtained result in the restriction map of the 7.5 kB insert depicted in FIG. 3. It was completely sequenced (Sanger et al. 1977) and contains inter alia the nucleotide sequence ID NO: 1. The derived amino acid sequence (SEQ ID NO: 2) in turn contains the peptides YGIEGLNNLEAL and AKEDANSTIEAED (SEQ ID NO: 3 and 4), which were found after tryptic digestion of the purified and blotted L-pantolactone hydrolase from *Burkholderia caryophylli* Lu681 and *Agrobacterium radiobacter* Lu5351 (see Examples 4 and 5).

Database comparisons (Genbank, EMBL, SwissProt, date May 7, 1999, [Sptrembel] and Janurary 5, 1999 [PIR]) for the nucleotide sequence and the derived amino acid sequence revealed only a small homology with a group of hypothetical proteins and with certain tetracycline cyclases from *streptomycetes* (Tab. 5). In particular, the motif with the consensus sequence HTGTHVDAP is highly conserved in all proteins. In addition, a homology of 48% (38% identical amino acids) was found with the isatin hydrolase from *Pseudomonas putida* WW2 (WO 94/09175), which likewise contains said sequence motif. Since no homology was found with other lactonases, esterases or lipases, the L-pantolactone hydrolases which have been found comprise a new class of enzymes. The sequence comparisons suggest a remotely related phylogenetic family to which said hypothetical proteins and tetracycline cyclases, and the isatin hydrolase, also belong.

10. L-pantolactone hydrolysis by *E. coli* XL1Blue pKS+681

A full inoculating loop of *E. coli* XL1Blue pKS+681 was grown (overnight, 37° C.) on an LB plate with ampicillin (100 µg/ml), IPTG (0.2 mM) and X-Gal (80 mg/l) and then resuspended (OD600=2.5) in 0.5 ml of Tris-HCl pH 7.0 and 50 mM D,L-pantolactone. A corresponding *E. coli* XL1Blue pBluescriptKS+-sample (OD600=2.5) was a useful comparison. After 1 h, the cells were centrifuged down and D,L-pantolactone, D,L-, D-, and L-pantoic acid were determined by HPLC analysis. Tab. 6a shows the activities and ee values for the various samples. The suspension had an activity of >90 U/L. However, no significant activity was evident in liquid culture batches (cf. Example 12).

11. Expression cloning of the L-pantolactone hydrolase in *E. coli* XL1Blue pKK223-3

On the basis of the nucleotide sequence SEQ ID NO: 1, the oligonucleotides 5'-CCGGAATTCATGTGCAA-CAACTGC (P1) and 5'-CCCAAGCTTCAGACCAGGGC-CAGAA (P2) were derived as primers for a PCR amplification of the L-pantolactone hydrolase gene under the following conditions: 20 mM Tris/HCl pH 8.8, 2 mM $MgSO_4$, 10 mM KCl, 10 mM $(NH_4)_2SO_4$, 0.1% Triton X-100, 0.1 mg/ml BSA, 25 mM each dNTP, 0.96 µg/ml pKS+681, P1 and P2 each 2.2 µg/ml, 25 U/ml Pfu polymerase (Stratagene, LaJolla, Calif.); the PCR parameters were as follows: 95° C. 1 min, 55° C. 1 min, 72° C. 2.5 min, 30 cycles. The resulting PCR product (0.8 kB) was cut with EcoRI and HindIII and ligated into pKK223-3 (Pharmacia, Freiburg) which had been cut with EcoRI and HindIII and dephosphorylated. The ligation mixture was transformed into *E. coli* XL1 Blue or TG1 (Stratagene, Lajolla, Calif.; DSMZ, Braunschweig, DSMZ-No. 6056, Inoue et al, 1990, Gene 96:23–28). The tansformants [sic] were plated out on LB-amp plates and incubated overnight. A filter replication and a subsequent activity assay were carried out on this transformation plate in analogy to Example 8, identifying about 100 intensely yellow clones. Ten were analyzed by mini preparation and restriction digestion (EcoRI-HindIII, EcoRI-HindIII-BamHI) of the plasmid DNA (Maniatis, T., Molecular Cloning: A laboratory [sic] manual, 1989). They contained the plasmid pKK681 which is depicted in FIG. 4.

12. L-pantolactone hydrolysis by *E. coli* XL1Blue pKK681

*E. coli* XL1Blue pKK681 was grown in 30 ml LB medium with ampicillin (100 µg/ml) and IPTG (0.5 mM) at 37° C. overnight, harvested and washed in Tris-HCl buffer (50 mM, pH 7.0) and resuspended (3 ml of 50 mM Tris/HCl pH 7.0). 0.25 ml of the suspension was mixed with 150 mM L-pantolactone, 150 mM Pipes pH 7.0 ad 0.5 ml distilled water, and incubated at 30° C. for 3 h.

In parallel, 0.25 ml of the suspension was mixed with 50 mM D,L-pantolactone, 50 mM Tris pH 7.0 ad 0.5 ml distilled water, and incubated for 3 h. In addition, 2 ml of the suspension were mixed with 300 mM D,L-pantolactone, 50 mM Tris pH 6.8 ad 20 ml distilled water, and incubated titrating with 4 M NaOH to pH 6.8 for 3 h. Samples were taken after 1 h and after 3 h, the cells were removed, and the supernatant was investigated for D,L-pantolactone, D,L-, D-, and L-pantoic acid. Tab. 6b shows the activities and ee values of the various samples. The overnight culture (1x concentrated) thus has an activity of 90 to 150 U/l.

On induction of *E. coli* XL1Blue pKK681 in the early exponential growth phase (OD600=0.6, +0.5 mM IPTG) the corresponding cells have an activity of about 480 U/l in the late exponential phase (OD600=4.1) after incubation at 37° C. for 5 h.

13. Expression cloning of the L-pantolactone hydrolase in *E. coli* TG1 pDHE19

On the basis of the nucleotide sequence SEQ ID NO: 1, the oligonucleotides 5'-CAGGATGCCATATGTGCAA-CAACTGC (P1) and 5'-CCCAAGCTTCAGACCAGGGC- CAGAA (P2) were derived as primers for a PCR amplification of the L-pantolactone hydrolase gene under the following conditions: 20 mM Tris/HCl pH 8.8, 2 mM $MgSO_4$, 10 mM KCl, 10 mM $(NH_4)_2SO_4$, 0.1% Triton X-100, 0.1 mg/ml BSA, 25 mM each dNTP, 0.96 µg/ml pKS+681, P1 and P2 each 2.2 µg/ml, 25 U/ml Pfu polymerase (Stratagene, LaJolla, Calif.); the PCR parameters were as follows: 95° C. 1 min, 55° C. 1 min, 72° C. 2.5 min, 30 cycles. The resulting PCR product (0.8 kB) was cut with NdeI and HindIII and ligated into pDHE19 (Prof. Mattes, Stuttgart) which had been cut with NdeI and HindIII and dephosphorylated. The ligation mixture was transformed into *E. coli* XL1 Blue or TG1 (Stratagene, Lajolla, Calif.; DSMZ, Braunschweig, DSMZ-No. 6056, Inoue et al, 1990, Gene 96: 23–28). The transformants were plated out on LB-ampicillin plates and incubated overnight. A filter replication on LB-ampicillin (100 µg/ml)/rhamnose (2 g/l) plates (LB=Luria Broth) and a subsequent activity assay were carried out on this transformation plate in analogy to Example 8, identifying about 100 intensely yellow clones. Ten were analyzed by mini preparation and restriction digestion (NdeI-HindIII, NdeI-HindIII-BamHI), and sequence analysis of the plasmid DNA (Maniatis, T., Molecular Cloning: A labaratory [sic] manual, 1989). They contained the plasmid pDHE681 which is depicted in FIG. 5.

14. L-pantolactone hydrolysis by *E. coli* TG1 pDHE681

*E. coli* TG1 pDHE681 was grown in 14 l of minimal medium with 40 g/l glycerol and 2.5 g/l rhamnose at 37° C. for 6 to 7 h, harvested and washed in Tris/HCl buffer (50 mM, pH 7.0) and resuspended ad 1.4 l of buffer. The activity of the one-fold concentrated cell suspension in the standard assay (150 mM Pipes pH 7.0, 150 mM L-pantolactone, 30° C., 1 h) was 680 to 2700 U/l or 60 to 160 g/DBM.

10 ml of the 10-fold concentrated suspension were incubated with 50 mM D,L-pantolactone in 50 mM Tris/HCl pH 7.0 (batch volume 20 ml) at 30° C. titrating with 4 M NaOH to pH 7.0. The conversion and the ee were determined by HPLC analysis after 0.4 h and 3 h (0.4 h: c=48%, ee=92%; 3 h: c=58%, ee=72% for L-pantoic acid). This corresponds to D-pantolactone with ee values of 84% and 100% respectively.

15. Preparation of D-pantolactone by hydrolysis with *E. coli* TG1 pDHE681

3 g of D,L-pantolactone were dissolved in 10 ml $H_2O$ and titrated to pH 6.5 with 4 M NaOH. After adding 5 to 10 ml of *E. coli* TG1 pDHE681 cell suspension (Example 14) and making up to 20 ml with $H_2O$, the reaction was incubated at 30° C., titrating to pH 6.8, for 15 to 22 h. Alternatively a further 0 to 2 ml of cell suspension was added and incubation was continued for 3 h, or 3×5 ml of cell suspension were added and incubation was continued for 90 h. FIG. 6 shows the course on the basis of the NaOH consumption. The ee values achieved for D-pantolactone were from 71 to 97%, depending on the conversion and incubation time. The cells from the 22 ml batches were then centrifuged down and washed with 5 ml of 50 mM Tris-HCl pH 7.0, and the supernatants were combined (20 to 25 ml) and extracted 3× with one volume of ethyl acetate. The organic phase was dried after addition of 10 g of $Na_2SO_4$ (anhydrous) at room temperature for 1 h. The precipitate was filtered off and washed 1× with ethyl acetate, and the filtrate was evaporated at 40° C. for 3 h. The viscous residue was weighed and analyzed by HPLC, GC, GC-MS and H-NMR (Tab. 7). It contained pure D-pantolactone (ee 71 to 87% after 50 to 52% conversion).

The aqueous phase (21 ml; Na L-pantoate) was adjusted to pH 1 with about 5 ml of 3 M $H_2SO_4$, heated at 80° C. for 15 min and mixed with 8 g of anhydrous $Na_2SO_4$. The resulting L-pantolactone was analogously extracted 3× with one volume of ethyl acetate, dried with $Na_2SO_4$ and evaporated. For recycling to the hydrolysis, the L-pantolactone melt can be racemized by heating after addition of NaOH in the presence of small amounts of Na L-pantoate (180° C., 3 h).

16. Preparation of D-pantolactone by hydrolysis with L-pantolactone hydrolase from *E. coli* strains L-Pantolactone hydrolase was obtained directly from fermentation broth from *E. coli* (TG1 pDHE681 or preferably strains which coexpress chaperones such as, for example, GroEL) by cell disruption (2×1000 bar in a microfluidizer), removal of cell detritus (9000 g at 10° C. for 20 min), 10-fold concentration by crossflow filtration (Hämoflow F60, Fresenius, membrane with exclusion of about 10 kDa) and heat-precipitation (20 min 60° C., 20 min RT-10° C., centrifugation) and concentrated to a specific activity of about 3000 U/g of protein. This 10× homogenate had an activity of 63–100000 U/l and a protein concentration of 20–30 g/l.

The racemate resolutions of 2.3 M D,L-pantolactone (30% w/v) with heat-precipitated homogenate (16000 U/l, 6 g/l protein) were carried out at 30° C. in 0.75 to 1.0 l batches titrating with 4 to 10 M NaOH (pH 7.5) with slight buffering (6 to 20 mM $NaHCO_3$). After incubation overnight, the enzyme was separated from the product-containing solution by cross flow filtration (Hamoflow F40, Fresenius, membrane with exclusion of about 10 kDa) of the mixture, washed 1 or 2× with deionized water and concentrated. The enzyme was then employed anew under the above conditions. A test of the useful life showed a doubling of the residence time necessary for an ee of >90% (D-PL) from 12 to 24 h after 6 d (FIG. 7). It ought to be possible to reduce the losses of activity by using larger volumes (e.g. 10 l batch for the F40 cartridge).

Workup of racemate resolution mixtures with homogenate (50.8% conversion, 92.5% ee) took place by extraction with 5×1 vol. of MTBE. 43% D-pantolactone with 91.4% ee and 98.2% purity ($GC_{int.st.}$; based on 100% racemate) were [lacuna]. After heating (65° C./15 min) with sulfuric acid (concentrated, 25 ml) and extraction again with MTBE (5×1 vol), 53% L-pantolactone were obtained with 62.3% ee and 98.2% purity ($GC_{int.st.}$). Protein or DNA impurities were undetectable by standard methods.

NaOH data from day 6 not available. 50.4% conversion, 89.8% ee at 1390 min (23.17 h).

Samples from day 7 not available, which is why there are no analytical data.

17. Preparation of D-pantolactone by hydrolysis with immobilized L-pantolactone hydrolase L-Pantolactone hydrolase was isolated as in Example 16 and bound to various carrier materials such as the commercially available EupergitC (Röhm GmbH, Darmstadt) or Deloxan DAPIII (Degussa, Frankfurt).

EupergitC

Eupergit is a carrier material activated by epoxy groups. The protein is thus mainly fixed covalently to amino groups.

Homogenate was firstly subjected to a precipitation by heat treatment. 1.1 l of homogenate were incubated in amounts each of 550 ml at 60° C. for 30 minutes and then cooled by placing on ice for 20 minutes. This solution was centrifuged (8000 rpm, GS3 rotor, 1 hour) in order to remove denatured protein. The supernatant was then concentrated on a Hamoflow F40 cartridge and the buffer was changed to 20 mM HEPES buffer, pH 7.5. There is no restriction on the choice of the amount of protein per g of Eupergit. In the following example, 7.2 g of protein were diluted in 270 ml of buffer with 30 ml of 1M potassium phosphate buffer pH 7.0 and salted down with 17.5 g of solid NaCl. The large amount of salt promotes binding of the protein to the carrier. The pH was adjusted to exactly pH 6.8, and then 15 g of dry Eupergit were added to this solution. The solution was agitated at room temperature for 17 hours. The reaction mixture was then filtered with suction through a glass funnel, and the carrier was washed with water. The moist material weighed about 60 g. 10 mM phosphate buffer, pH 7.5, was used for storage.

Deloxan DAPIII, with and without reduction

Deloxan is a silicate modified with amino groups. These amino groups can be activated with glutaraldehyde to form a Schiff's base. The excess aldehyde is then washed off, and the protein is added to the activated carrier. The free amino groups of the protein react with the still free aldehyde of the bound glutaraldehyde to form a second Schiff's base. This protein immobilized in this way is ready for use. The Schiff's base is, however, prone to hydrolysis so that the protein is slowly leached off the carrier in aqueous solution. This can be avoided by reduction with sodium borohydride. This entails converting the Schiff's base into a secondary amine. The precondition for this is that the enzyme is stable to reduction with sodium borohydride.

Heat precipitation of the homogenate as for the immobilization on EupergitC.

Activation:

140 g of Deloxan DAPIII were washed with water and then with 1.5 l of 0.1M sodium phosphate buffer, pH 6, and 1.5 l of 0.1 M sodium phosphate buffer, pH 7.5, and were resuspended. To this were added 560 ml of a 2.5% strength glutaraldehyde solution (pH 7.5 corrected in the same buffer) and reacted for 3 to 4 hours. The carrier became orange-red. The activated carrier was then washed with 6 l of water and resuspended in 1 l of sodium phosphate buffer (pH 7.5).

10000 U (about 2.7 g of protein) of L-pantolactone hydrolase, for example, were added to 40 g of activated Deloxan. The protein was incubated with the activated carrier at room temperature for 18 hours. The solution was separated from the carrier on a glass suction funnel. The carrier was washed several times with water and then with 1 l of 0.1M phosphate buffer, pH 7.2 and 1 M NaCl. Half of the carrier was removed (without reduction). The other half was again washed with water and then added to 0.1 M sodium borate buffer, pH 7.2.

Reduction by sodium borohydride:

0.4 g of sodium borohydride (0.5%) was added to the carrier resuspended in 80 ml of borate buffer, and the mixture was agitated at room temperature for 3 hours. During this, the carrier material became pale yellow again. The carrier was filtered off with suction on a glass funnel and washed with 400 ml of borate buffer. The carrier was then washed with 1 l of water and then taken up in 20 mM phosphate buffer.

Racemate resolution

For racemate resolution of 2.3 M D,L-pantolactone (30% w/v) with immobilizates, the latter were stirred in 40 ml batches at 30° C., titrating with 10 M NaOH (pH 7.5) in 10 mM NaHCO$_3$, until the ee for D-pantolactone was about 90% (25 to 60 h). The biocatalyst was separated from the product after each batch by filtration (filtration of the reaction mixture with suction through an HPLC eluent filter) and recovered, where appropriate washing 3× (deionized water).

TABLE 1a

Pantoic acid formation (3 h)

| LU No. | Genus | Species | PA [mM] | PA [g/l] | Aspec. [sic] [U/g] | ee [%] uncorr. | ee [%] corr. | Direct hydrolysis (+) or else oxid.-red. (−) |
|---|---|---|---|---|---|---|---|---|
| 22 | Agrobacterium | tumefaciens | 5.6 | 0.8 | 1.5 | 94.6 | 97.0 | + |
| 5351 | Agrobacterium | radiobacter | 4.8 | 0.7 | 1.6 | 97.3 | 100.0 | + |
| 3215 | Apiotrichum | humicola | 7.9 | 1.2 | 1.5 | 82.0 | 77.8 | + |
| 7953 | Beauveria | amorpha | 5.9 | 0.9 | 1.0 | 68.5 | 72.1 | + |
| 680 | Burkholderia | solanacearum | 2.1 | 0.3 | 0.5 | 70.3 | 80.9 | + |
| 681 | Burkholderia | caryophylli | 6.7 | 1.0 | 2.0 | 96.0 | 98.7 | + |
| 683 | Pseudomonas | diminuta | 6.0 | 0.9 | 1.1 | 98.0 | 100.0 | + |
| 863 | Pseudomonas | sp. | 7.3 | 1.1 | 1.9 | 92.0 | 94.0 | + |
| 4314 | Psilocybe | coprohila [sic] | 2.4 | 0.4 | 0.5 | 65.3 | 74.3 | + |

PA, pantoic acid
ee values refer to the formation of (L)-pantoic acid
ee, enantiomeric excess, corr., ee corrected by subtraction of the pantoic acid formed by chemical hydrolysis (blank)

TABLE 1b

Pantoic acid formation

| LU No | Genus | Species | ee [%] | ee [%] corr. | t [min] | Conversion [%] | E (corr.) |
|---|---|---|---|---|---|---|---|
| 22 | Agrobacterium | tumefaciens | 90.2 | 94.5 | 1352 | 6.8 | 38 |
| 5351 | Agrobacterium | radiobacter | 93.8 | 96.5 | 1161 | 52.5 | >229 |
| 3215 | Apiotrichum | humicola | 79.4 | 79.1 | 91 | 54.0 | 29 |
| 7953 | Beauveria | amorpha | 31.3 | 33.8 | 288 | 20.6 | 3 |
| 680 | Burkholderia | solanacearum | 78.1 | 81.3 | 1318 | 54.1 | 37 |
| 681 | Burkholderia | caryophylli | 94.7 | 97.6 | 187 | 44.6 | 198 |
| 683 | Pseudomonas | diminuta | 96.3 | 98.7 | 185 | 48.5 | 524 |

TABLE 1b-continued

|  |  |  | Pantoic acid formation | | | | |
|---|---|---|---|---|---|---|---|
| LU No | Genus | Species | ee [%] | ee [%] corr. | t [min] | Conversion [%] | E (corr.) |
| 863 | *Pseudomonas* | sp. | 89.5 | 91.9 | 1256 | 47.9 | 64 |
| 4314 | *Psilocybe* | coprophila | 42.6 | 49.7 | 1063 | 15.6 | 3 | ee values relate to the formation of (L)-pantoic acid
ee, enantiomeric excess; E, enantioselectivity; corr., ee or E corrected by subtraction of the pantoic acid formed by chemical hydrolysis (blank)

TABLE 2

Purification of the L-pantolactone hydrolase from Lu5351

| Sample | Vol. [L] | Activity [U/L] | Total act. [U] | Yield of activ. [%] | Protein [g/L] | Total prot. [g] | Yield of prot. [%] | Spec. act. [U/g prot.] |
|---|---|---|---|---|---|---|---|---|
| Fermenter | 28.0 | 2.0 | 56.8 | — | — | — | — | — |
| Before cell disruption | 1.44 | 20.0 | 28.8 | 100.0 | — | — | — | — |
| Cell disruption 1st passage | 1.44 | 5.5 | 7.9 | 27.5 | — | — | — | — |
| Cell disruption 2nd passage | 1.44 | 52.2 | 75.1 | 260.8 | — | — | — | — |
| After cell disruption suspension | 1.86 | 57.3 | 106.6 | 370.3 | — | — | — | — |
| After cell disruption supernatant | 1.82 | 84.7 | 154.1 | 535.0 | 8.52 | 15.51 | 100.0 | 9.9 |
| Supernatant after $MnCl_2$ | 1.8 | 72.0 | 129.6 | 450.0 | 10.32 | 18.58 | 119.8 | 7.0 |
| Phenyl-Sepharose loading | 2.04 | 10.7 | 21.9 | 76.0 | 7.2 | 14.69 | 94.7 | 1.5 |
| Phenyl-Seph. peak | 0.16 | 87.0 | 13.9 | 48.3 | 7.82 | 1.251 | 8.1 | 11.1 |
| Q-Seph. peak | 0.12 | 83.5 | 10.0 | 34.8 | 0.36 | 0.043 | 0.3 | 231.9 |
| Superdex loading | 0.012 | 605.0 | 7.3 | 25.2 | — | — | — | — |
| Superdex peak | 0.04 | 41.3 | 1.7 | 5.7 | 0.53 | 0.021 | 0.1 | 78.0 |

TABLE 3a

Substrate specificity of the L-pantolactone hydrolase from Lu681

| Substrate | Concentration (mN) | Activity |
|---|---|---|
| S-Pantolactone | 150 | ++ |
| D-Pantolactone | 150 | − |
| γ-Butyrolactone | 150 | + |
| γ-Valerolactone | 150 | + |
| δ-Valerolactone | 50 | + |
| ε-Caprolactone | 150 | ++ |
| (+/−)δ-Decanolactone | 15 | − |
| δ-Nonalactone | 75 | + |
| Ethyl D(+)-lactate | 150 | + |
| Ethyl (L)(−)-lactate | 150 | ++ |
| D-Galactono-γ-lactone | 150 | + |
| L-Galactono-γ-lactone | 150 | ++ |
| L-(+)-Gulono-γ-lactone | 150 | + |
| D-(−)-Gulono-γ-lactone | 150 | + |
| 1,2-O-Dilauryl-rac-glycero-3-glutaric acid resorufin ester | 0.25 | (+) |
| 5-Hydroxy-2-coumaranone | 2.5 | + |
| α-Naphthyl acetate | 2.5 | (+) |
| Isatin | 10 | + |

++: >50 U/l
+: >5 U/l
(+): >0.5 U/l
−: <0.5 U/l

TABLE 3b

Substrate specificity of the L-pantolactone hydrolase from Lu5351

| Substrate | Concentration (mN) | Activity |
|---|---|---|
| S-Pantolactone | 150 | ++ |
| D-Pantolactone | 150 | (+) |
| γ-Butyrolactone | 150 | ++ |
| γ-Valerolactone | 150 | ++ |
| δ-Valerolactone | 50 | ++ |
| ε-Caprolactone | 150 | ++ |
| (+/−)δ-Decanolactone | 15 | ++ |
| δ-Nonalactone | 75 | ++ |
| Ethyl D(+)-lactate | 150 | + |
| Ethyl L(−)-lactate | 150 | ++ |
| D-Galactono-γ-lactone | 150 | ++ |
| L-Galactono-γ-lactone | 150 | ++ |
| L-(+)-Gulono-γ-lactone | 150 | ++ |
| D-(−)-Gulono-γ-lactone | 150 | ++ |
| 1,2-O-Dilauryl-rac-glycero-3-glutaric acid resorufin ester | 0.25 | (+) |
| Dihydrocumarin | 2.5 | + |
| α-Naphthylacetate | 2.5 | (+) |
| Isatin | 10 | (+) |

++: >50 U/l
+: >5 U/l
(+): >0.5 U/l
−: <0.5 U/l

TABLE 3c

Lipase activity of the purified L-pantolactone hydrolase from Lu681

| L-PL Activity [U/l] | ΔE (λ = 572) | Lipase activity [U/l] | Activity [%] |
|---|---|---|---|
| 481.82 | 0.50 | 0.19 | 0.04 |
| 240.91 | 0.40 | 0.15 | 0.06 |
| 120.45 | 0.18 | 0.07 | 0.05 |
| 60.23 | 0.05 | 0.02 | 0.03 |

TABLE 4a

Effects of various added substances on the activity of L-pantolactone hydrolase from *Burkholderia caryophylli* Lu681 in the standard assay

| Substance | Concentration [mM] | Relative Activity |
|---|---|---|
| no addition | — | 100% |
| EDTA | 1 | 97% |
| Citric acid pH 6.4 | 30 | 97% |
| o-Phenanthroline | 1 | 95% |
| $HgCl_2$ | 1 | 133% |
| pCMBS | 1 | 108% |
| DTT | 1 | 99% |
| PMSF | 1 | 113% |
| DIFP | 1 | 115% |
| Pepstatin | 1 | 117% |
| $H_2O_2$ | 1% | 95% |
| KCN | 1 | 102% |
| KCl | 1 | 99% |
| $NH_4Cl$ | 1 | 100% |
| $MgCl_2$ | 1 | 99% |
| $CaCl_2$ | 1 | 101% |
| $MnCl_2$ | 1 | 100% |
| $CoCl_2$ | 1 | 97% |
| $FeCl_2$ | 1 | 104% |
| $NiCl_2$ | 1 | 96% |
| $ZnCl_2$ | 1 | 113% |
| SDS | 1% | 102% |

TABLE 4a-continued

Effects of various added substances on the activity of L-pantolactone hydrolase from *Burkholderia caryophylli* Lu681 in the standard assay

| Substance | Concentration [mM] | Relative Activity |
|---|---|---|
| CHAPS | 0.1% | 104% |
| Triton | 0.1% | 104% |
| Isopropanol | 10% | 93% |
| Acetonitrile | 10% | 119% |
| MeOH | 10% | 100% |

TABLE 4b

Effects of various added substances on the activity of the L-pantolactone hydrolase from *Agrobacterium radiobacter* Lu5351 in the standard assay

| Substance | Concentration [mM] | Relative Activity |
|---|---|---|
| No addition | — | 100% |
| EDTA | 1 | 97% |
| DIFP | 1 | 92% |
| CHAPS | 0.1% | 100% |
| SDS | 1% | 74% |
| pCMBS | 1 | 112% |
| DTT | 1 | 106% |
| $HgCl_2$ | 1 | 170% |
| $FeCl_2$ | 1 | 108% |
| $ZnCl_2$ | 1 | 99% |
| $MgCl_2$ | 1 | 114% |
| $CaCl_2$ | 1 | 105% | pCMBS = p-Chloromercuribiphenylsulfonic [sic] acid
DTT = Dithiothreitol
SDS = Sodium dodecyl sulfate
EDTA = Ethylenediaminetetraacetic acid
DIFP = Diisopropyl fluorophosphate
CHAPS = ([3-Cholamidopropyl]-dimethylammonio)-1-propane-sulfonate

TABLE 5

Homologies of the L-pantolactone hydrolase amino acid sequence from Lu681 according to gap[4] and bestfit[5] searches

| Position in the pKS+681 insert (bp) | Aa | Homolog | Reference /Acc. No. | Organism | Gap homology (% aa) | Gap identity (% aa) | Bestfit homology (% aa) | Bestfit identity (% aa) |
|---|---|---|---|---|---|---|---|---|
| 1498–2304 | 269 | Isatin hydrolase | WO9119175 | *Pseudomonas putida* | 47.9 | 37.4 | 48.1 | 37.6 |
| | | Hypothetical protein | B69206 | *M. thermoautotrophicum* | 42.6 | 29.8 | 43.0 | 30.1 |
| | | | D70817 | *M. tuberculosis* | 37.1 | 28.5 | 41.7 | 31.5 |
| | | | B72430 | *T. maritima* | 45.4 | 31.9 | 45.9 | 32.2 |
| | | | G69399 | *Archaeoglobus fulgidus* | 35.5 | 26.3 | 42.1 | 30.3 |
| | | | S39964 | *S. griseus* | 39.6 | 29.8 | 42.0 | 32.1 |
| | | | S75497 | *Synechocystis sp.* | 36.3 | 26.8 | 48.1 | 32.9 |
| | | | T06135 | *A. thaliana* | 31.3 | 23.1 | 46.3 | 35.0 |
| | | | T05418 | *A. thaliana* | 33.0 | 23.7 | 42.0 | 29.0 |
| | | Polyketide synthase | O68500 | *S. peuceticus* | 42.7 | 32.6 | 46.6 | 37.5 |
| | | Tetracycline synthase | O86485 | *S. argillaceus* | 43.2 | 34.9 | 44.6 | 35.2 |
| | | ORF | Q54196 | *S. griseus* | 39.6 | 29.8 | 42.0 | 32.1 |

[4]Needleman & Wunsch (1970), J. Mol. Biol. 48, 443–453
[5]Smith & Waterman (1981), Adv. Appl. Math. 2, 482–489

TABLE 6

Expression of the L-pantolactone hydrolase in *E. coli* XL1 Blue a) XL1 Blue pKS+681 and pKS+ (negative control)

| Plasmid | Assay conditions | OD600 i.a. | Δ PA/mM 1h | A/U/l | ee (L-PA) |
|---|---|---|---|---|---|
| pKS+681 | 300 mM D,L-PL/1.1 M Tris/HCL [sic] pH 7.0 | 2.5 | 5.55 | 92.5 | 79.7 |
| pKS+ | 300 mM D,L-PL/1.1 M Tris/HCL [sic] pH 7.0 | 2.5 | 0.21 | 3.5 | n.d. |
| pKS+681 | 300 mM D,L-PL/1.1 M Tris/HCL [sic] pH 7.0, 1% SDS | 2.5 | 7.79 | 132.8 | n.d. |
| pKS+ | 300 mM D,L-PL/1.1 M Tris/HCL [sic] pH 7.0, 1% SDS | 2.5 | 0.02 | 0 | n.d. | b) XL1 Blue pKK681

| Batch | Assay conditions | DBM i.a./g/l | Δ PA/mM 1h | Δ PA/mM 3h | A/U/l | ee (L-PA) |
|---|---|---|---|---|---|---|
| 1 | 50 mM D,L-PL, 50 mM Tris/HCl pH 7.0 | 8.6 | n.d. | 5.2 | 28 | 95.3 |
| 2 | 150 mM L-PL, 150 mM Pipes pH 7.0 | 8.6 | 46 | 46 | 760 | (—) |
| 3 | 300 mM D,L-PL, 50 mM Tris/HCl pH 6.8, Titration with 4M NaOH | 1.7 | 5.6 | 16.5 | 92 | 91.3 | n.d., not determined

TABLE 7a

Workup of D-pantolactone

| Total yield | 69.00% |
|---|---|
| Purity (GC-MS) | >98.00% |
| Purity (H-NMR) | >95.00% |
| Water content | <0.40% |

TABLE 7b

Workup of L-pantolactone

| Total yield | 85.00% |
|---|---|
| Purity (GC-MS)* | >95.00% |
| Purity (H-NMR) | >97.00% |
| Water content | <0.40% |

What is claimed is:

1. An isolated nucleic acid sequence which codes for a polypeptide having L-pantolactone hydrolase activity, and which is useful for the preparation of D-pantolactone, selected from the group of:
    a) a nucleic acid sequence having the sequence depicted in SEQ ID NO:1,
    b) nucleic acid sequences which, as a result of the degeneracy of the genetic code, are derived from the nucleic acid sequence depicted in SEQ ID NO:1,
    c) derivatives of the nucleic acid sequence depicted in SEQ ID NO:1 which code for polypeptides having at least 80% homology at the amino acid level with the amino acid sequences depicted in SEQ ID NO:2, with negligible reduction in the enzymatic action of the polypeptides.

2. An amino acid sequence encoded by a nucleic acid sequence as claimed in claim 1.

3. An amino acid sequence as claimed in claim 2, encoded by the sequence depicted in SEQ ID NO:1.

4. A nucleic acid construct comprising a nucleic acid sequence as claimed in claim 1, where the nucleic acid sequence is linked to one or more regulatory signals.

5. A vector comprising a nucleic acid sequence as claimed in claim 1 or a nucleic acid construct comprising a nucleic acid sequence as claimed in claim 1, where the nucleic acid sequence is linked to one or more regulatory signals.

6. A microorganism comprising at least one nucleic acid sequence as claimed in claim 1, or at least one nucleic acid construct comprising a nucleic acid sequence as claimed in claim 1 in which the nucleic acid sequence is linked to one or more regulatory signals, or a vector comprising the nucleic acid sequence or the nucleic acid construct.

7. A microorganism as claimed in claim 6, which is a Gram-negative bacterium.

8. A microorganism as claimed in claim 6, which is a bacterium from the group of α-proteobacteria, β-proteobacteria or γ-proteobacteria.

9. A microorganism as claimed in claim 6, which is a bacterium from the family of Enterobacteriaceae, Pseudomonadaceae or Rhizobiaceae.

10. A microorganism as claimed in claim 6, which is a bacterium from the genera *Agrobacterium, Pseudomonas, Burkholderia, Salmonella* or *Escherichia*.

11. L-pantolactone hydrolase having the following properties:
    a) conversion of L-pantolactone into the corresponding acid,
    b) pH stability: L-pantolactone hydrolase is stable in a pH range from 4 to 10
    c) pH optimum: 7.2 to 7.6
    d) temperature optimum: about 70° C. to 75° C.
    e) no inhibition of the activity by EDTA.

12. A process for preparing D-pantolactone, which comprises the following reaction steps:
    a) converting racemic pantolactone in the presence of an L-pantolactone hydrolase having the following properties:
        1) conversion of L-pantolactone into the corresponding acid,
        2) pH stability: L-pantolactone hydrolase is stable in a pH range from 4 to 10
        3) pH optimum: 7.2 to 7.6
        4) temperature optimum: about 70° C. to 75° C.
        5) no inhibition of the activity by EDTA,
    an L-pantolactone hydrolase having an amino acid sequence encoded by a nucleic acid sequence as claimed in claim 1 or
    a microorganism comprising at least one nucleic acid sequence as claimed in claim 1, at least one nucleic acid construct comprising a nucleic acid sequence as claimed in claim 1 where the nucleic acid sequence is linked to one or more regulatory signals, or a vector comprising the nucleic acid sequence or the nucleic acid construct into D-pantolactone and L-pantoic acid and b) removing the D-pantolactone.

13. A process as claimed in claim 12, wherein the L-pantoic acid obtained in reaction step (b) is racemized and recycled to reaction step (a).

14. A process as claimed in claim 12, wherein the conversion of the racemic pantolactone is carried out in the presence of an immobilized L-pantolactone.

15. A process as claimed in claim 12, wherein the conversion of the racemic pantolactone is carried out in the presence of a growing, resting or disrupted microorganism.

16. A process as claimed in claim 12, wherein the microorganism is immobilized.

17. A process as claimed in claim 12, wherein the process is carried out in an aqueous reaction solution at a pH between 4 and 12.

18. A process as claimed in claim 12, wherein the process is carried out at a temperature between 0° C. and 95° C.

19. A process as claimed in claim 12, wherein the D-pantolactone is removed by extraction.

20. A process as claimed in claim 12, wherein the D-pantolactone has an optical purity of at least 90% ee.

* * * * *

UNITED STATES PATENT AND TRADEMARK OFFICE
CERTIFICATE OF CORRECTION

PATENT NO. : 6,998,258 B1  
APPLICATION NO. : 10/111451  
DATED : February 14, 2006  
INVENTOR(S) : Kesseler et al.

Page 1 of 1

It is certified that error appears in the above-identified patent and that said Letters Patent is hereby corrected as shown below:

In Claim 1, column 25, line 45 please delete:
"selected from the group of:" and substitute therefore:
-- selected from the group consisting of: --

In Claim 1, column 25, line 50 please delete:
"nucleic acid sequence depicted in SEQ ID NO:1," and substitute therefore:
-- nucleic acid sequence depicted in SEQ ID NO:1, and --

In Claim 1, column 25, line 53 please delete:
"least 80% homology at the amino acid level with the" and substitute therefore:
-- least 95% homology at the amino acid level with the --

In Claim 13, column 27, line 8 please delete:
"toic acid obtained in reaction step (b) is racemized and" and substitute therefore:
-- toic acid obtained is racemized and --

Signed and Sealed this

Twenty-eighth Day of November, 2006

JON W. DUDAS  
*Director of the United States Patent and Trademark Office*